United States Patent
Pohlmann et al.

(10) Patent No.: US 8,802,858 B2
(45) Date of Patent: Aug. 12, 2014

(54) FURAZANOBENZIMIDAZOLES AS PRODRUGS TO TREAT NEOPLASTIC OR AUTOIMMUNE DISEASES

(75) Inventors: Jens Pohlmann, Basel (CH); Felix Bachmann, Basel (CH)

(73) Assignee: Basilea Pharmaceutica AG, Basel (CH)

( * ) Notice: Subject to any disclaimer, the term of this patent is extended or adjusted under 35 U.S.C. 154(b) by 82 days.

(21) Appl. No.: 13/384,467

(22) PCT Filed: Jul. 26, 2010

(86) PCT No.: PCT/EP2010/060803
§ 371 (c)(1),
(2), (4) Date: Mar. 9, 2012

(87) PCT Pub. No.: WO2011/012577
PCT Pub. Date: Feb. 3, 2011

(65) Prior Publication Data
US 2012/0264792 A1    Oct. 18, 2012

(30) Foreign Application Priority Data
Jul. 27, 2009 (EP) .................................. 09166469

(51) Int. Cl.
*A61K 31/44*     (2006.01)
*C07D 413/04*   (2006.01)

(52) U.S. Cl.
CPC .................................. *C07D 413/04* (2013.01)
USPC ....................................... 546/269.4; 514/338

(58) Field of Classification Search
USPC ................................. 546/189, 208
See application file for complete search history.

(56) References Cited

U.S. PATENT DOCUMENTS
RE42,890 E * 11/2011 Eberle et al. .................. 548/125

FOREIGN PATENT DOCUMENTS
WO     2004103994     12/2004

OTHER PUBLICATIONS
The International Search Report and Written Opinion by the International Searching Authority, issued on Oct. 7, 2010, in the corresponding PCT application No. PCT/EP2010/060803.
Ten Tije et al., "Pharmacological effects of formulation vehicles: implications for cancer chemotherapy," Clinical Pharmacokinetics (2003), 42(7), 665-685).
Simplicio et al., "Prodrugs for Amines," Molecules 2008, 13, 519-547.
Stella et al., "Prodrugs: Challenges and Rewards," Publisher: (Springer, New York, N. Y.), USA. 2007, pp. 102-131.
Rautio et al., "Prodrugs: design and clinical applications," Nature Rev. Drug Discovery 2008, 7, 255-270.

* cited by examiner

*Primary Examiner* — Heidi Reese

(57) ABSTRACT

A compound of formula II

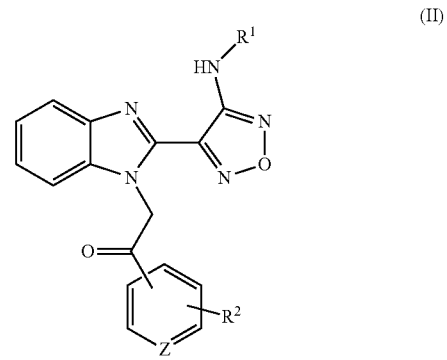

in which Z is C or N and the Z ring is optionally further substituted; $R^1$ is H, lower alkylcarbonyl, hydroxy-lower alkyl or cyano-lower alkyl; and $R^2$ is a group selected from (b), (c), and (d):

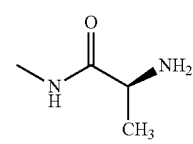

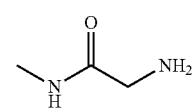

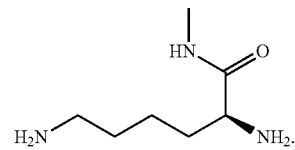

20 Claims, 1 Drawing Sheet

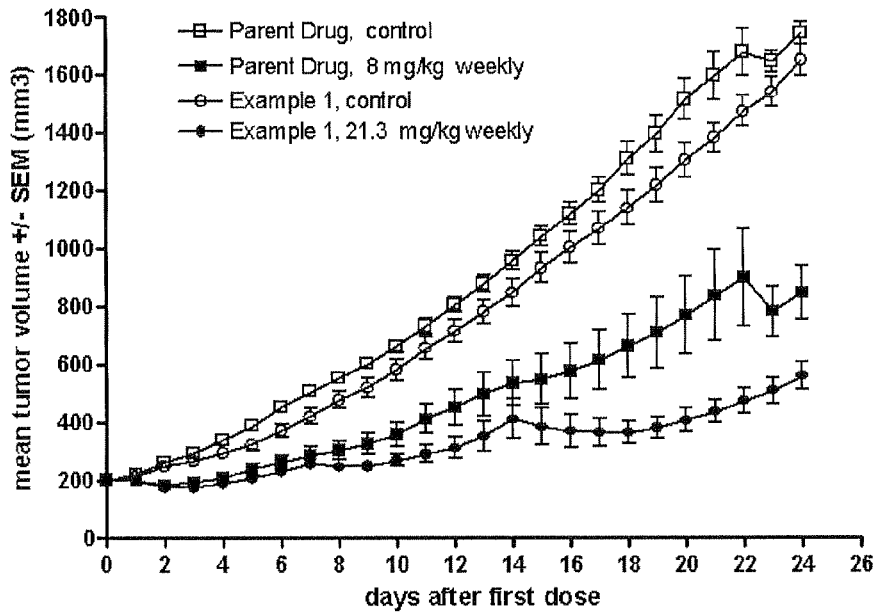
Figure 1: Anti-tumor activity of the prodrug of Example 1 versus its parent drug in SW480 colorectal cancer xenografts after once weekly intravenous application.
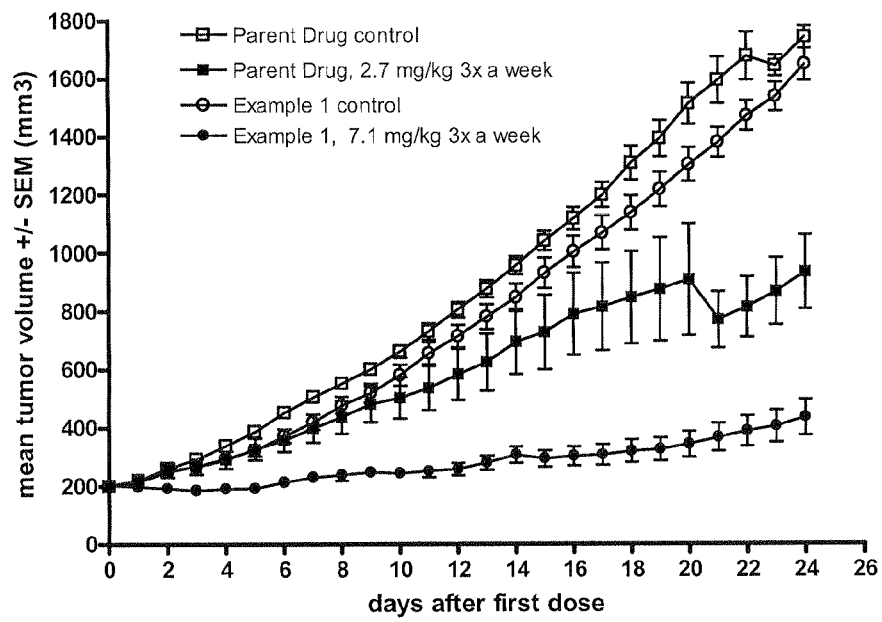
Figure 2: Anti-tumor activity of the prodrug of Example 1 versus its parent drug in SW480 colorectal cancer xenografts after 3 times weekly intravenous application.

FURAZANOBENZIMIDAZOLES AS PRODRUGS TO TREAT NEOPLASTIC OR AUTOIMMUNE DISEASES

This application is a National Stage Application of PCT/EP2010/060803 filed Jul. 26, 2010, which claims priority from European Patent Application 09166469.8 filed on Jul. 27, 2009. The priority of both said PCT and European Patent Application is claimed.

The invention relates to prodrugs of substituted furazanobenzimidazoles, processes for the preparation thereof and pharmaceutical compositions containing the same, the use thereof optionally in combination with one or more other pharmaceutically active compounds for the therapy of neoplastic diseases and autoimmune diseases.

Cancer is one of the leading causes of death in humans. Although a variety of drugs against neoplastic diseases have been developed and techniques are available such as surgery and radiation therapy, there is still a need for alternative and improved methods of treatment of neoplastic diseases.

Autoimmune diseases are associated with abnormal lymphoproliferation as a result of defects in the termination of lymphocyte activation and growth. Often, such diseases are associated with inflammation like rheumatoid arthritis, insulin dependent diabetes mellitus, multiple sclerosis, systemic lupus erythematosus and the like. The treatment of such diseases is focused on anti-inflammatory and immunosuppressive drugs which in numerous cases show severe side effects. Hence, there is a need for alternative drugs with a new mode of action showing less side effects.

Apoptosis is a term used to describe a series of cellular events which occur to bring about programmed cell death. There are various apoptotic pathways, some of which have been characterized, whereas others remain to be elucidated. If the balance between cell division and apoptosis is disturbed, life-threatening diseases including cancer, autoimmune disorders, neurodegenerative and cardiovascular diseases may occur.

In recent years it has become evident that programmed cell death (apoptosis) is as important to the health of a multicellular organism as cell division. By repeated cell division and differentiation throughout development or tissue repair, surplus or even harmful cells are generated. In order to maintain tissue homeostasis these cells have to be removed or killed. The delicate interplay between cell growth and apoptosis in an organism is mirrored in the complex molecular balance that determines whether an individual cell undergoes division, arrests in the cell cycle or commits to programmed cell death.

Dysregulation of cell proliferation, or lack of appropriate cell death, has wide ranging clinical implications. A number of diseases associated with such dysregulation involve hyperproliferation, inflammation, tissue remodeling and repair. Familiar indications in this category include cancers, restenosis, neointimal hyperplasia, angiogenesis, endometriosis, lymphoproliferative disorders, transplantation related pathologies (graft rejection), polyposis, loss of neural function in the case of tissue remodeling and the like. Such cells may lose the normal regulatory control of cell division, and may also fail to undergo appropriate cell death.

As apoptosis is inhibited or delayed in most types of proliferative, neoplastic diseases, induction of apoptosis is an option for treatment of cancer, especially in cancer types which show resistance to classic chemotherapy, radiation and immunotherapy (Apoptosis and Cancer Chemotherapy, Hickman and Dive, eds., Blackwell Publishing, 1999). Also in autoimmune and transplantation related diseases and pathologies compounds inducing apoptosis may be used to restore normal cell death processes and therefore can eradicate the symptoms and might cure the diseases. Further applications of compounds inducing apoptosis may be in restenosis, i.e. accumulation of vascular smooth muscle cells in the walls of arteries, and in persistent infections caused by a failure to eradicate bacteria- and virus-infected cells. Furthermore, apoptosis can be induced or re-established in epithelial cells, in endothelial cells, in muscle cells, and in others which have lost contact with extracellular matrix. These cells are potentially able to colonize other organs and therefore can develop into pathologies like neoplasias, endometriosis and the like.

WO2004/103994 discloses furazanobenzimidazole compounds of formula (I)

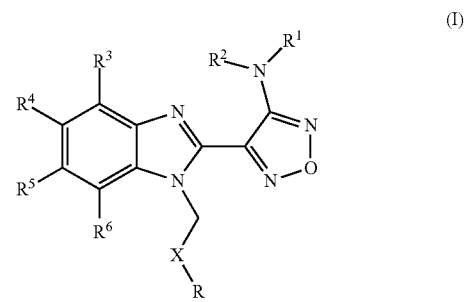

(I)

wherein R, $R^1$ to $R^6$ and X have certain broadly defined meanings as inducers of apoptosis in cancer cells.

The reference furthermore discloses that these compounds can be administered in the form of prodrugs which are broken down in the human or animal body to give the corresponding compound of formula (I) and mentions that among other types of prodrugs amides of naturally occurring amino acids, e.g. amides formed from the acid function of the amino acid and suitable amino groups of the compound of formula (I), are suitable as prodrugs.

The aqueous solubility of furazanobenzimidazoles like those exemplified in WO2004/103994 is generally low. This is a problem for the preparation of pharmaceutical compositions, especially compositions for parenteral administration. The reference suggests only very general to use an aqueous solution of a water-soluble salt of the compounds of formula (I) for parenteral administration.

It has now been found that selected amides derived from furazanobenzimidazoles of the afore-mentioned formula (I), wherein R represents an aryl or heteroaryl group substituted by at least one amino group, and a natural amino acid selected from glycine (Gly), alanine (Ala) and lysine (Lys) display significantly improved aqueous solubility and are cleaved in vivo to the parent aromatic or heteroaromatic amine, thereby acting as prodrugs. The increased aqueous solubility simplifies the preparation of pharmaceutical compositions and reduces the need for solubility enhancing excipients compared to the parent drug. This is of special advantage since these excipients can cause unwanted toxic effects (Excipient Toxicity and Safety; Weiner, Myra L.; Kotkoskie, Lois A.; Editors. (2000), Publisher: Dekker, New York, USA. Pharmacological effects of formulation vehicles: implications for cancer chemotherapy; ten Tije; Albert J.; Verweij, Jaap; Loos, Walter J.; Sparreboom, Alex; Clinical Pharmacokinetics (2003), 42(7), 665-685).

Specifically for the lysine (Lys) derived prodrug, a very strongly increased solubility is observed over an especially broad pH range and even at only slightly acidic conditions. These specific solubility properties of the lysine derivative also at higher pH values provide a particularly excellent flexibility in the preparation of pharmaceutically acceptable compositions. It was furthermore found in pharmacokinetic studies in mice, that the amide prodrugs derived from glycine (Gly), alanine (Ala) and lysine (Lys) provide significantly higher exposure of the animals to the parent drug (expressed as AUC (area under the curve) value) than those derived from other natural amino acids. For example, AUC values are more than 50 percent higher than the AUC values found after administration of amide prodrugs derived from other very similar natural amino acids like asparagine (Asn), serine (Ser), glutamine (Gln) or arginine (Arg).

Additionally, it was found that the specific Lys derived prodrug of Example 1 of this application is better tolerated, provides longer exposure of tumors to the drug and has a higher efficacy in animal tumor models at the maximum tolerated dose than the corresponding parent drug. These surprising effects suggest also a higher efficacy of this prodrug in the therapy of neoplastic diseases and autoimmune diseases.

In a full blood in vitro assay, an amino acid amide derived from the amino group at the furazane ring is converted less efficiently into the parent drug than the corresponding derivative with the amino acid amide being a substituent of the residue R in the afore-mentioned formula (I). This shows that not all amides derived from an amino group of the compound of formula (I) and a natural amino acid are equally well suited as prodrugs.

Various other types of amine prodrugs are described in the literature (e.g. A. L. Simplicio, J. M. Clancy, J. F. Gilmer, Molecules 2008, 13, 519-546; Prodrugs: Challenges and Rewards, [in: Biotechnol.: Phalli'. Aspects, 2007; 5(Pt. 2)] V. J. Stella, R. T. Borchardt, M. J. Hageman, R. Oliyai, H. Maag, J. W. Tilley, Editors, USA. 2007, pages 102-131, Publisher: (Springer, New York, N.Y.); J. Rautio, H. Kumpulainen, T. Heimbach, R. Oliyai, D. Oh, T. Jarvinen, J. Savolainen, Nature Rev. Drug Discovery 2008, 7, 255-270). However, not every potential prodrug is sufficiently converted into the parent drug in every case, which is exemplified with an amidine and a sulfamate derivative of the furazanobenzimidazoles, which do not give quantifiable plasma levels of the parent drug after administration in animal studies. This underscores further the challenge to identify for a given drug suitable prodrugs combining all required properties.

The present invention accordingly relates to compounds of formula (II)

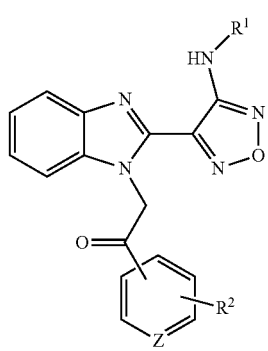

(II)

wherein

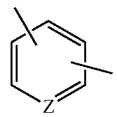

represents a divalent benzene residue which is unsubstituted or substituted by one or two additional substituents independently selected from lower alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; or wherein two adjacent substituents can be methylenedioxy; or a divalent pyridine residue (Z=N) which is unsubstituted or substituted additionally by lower alkyl, lower alkoxy, lower alkoxy-lower alkoxy, amino, optionally substituted by one or two substituents selected from lower alkyl, lower alkenyl and alkylcarbonyl, halo-lower alkyl, lower alkoxy-lower alkyl, or halogen;

$R^1$ represents hydrogen, lower alkylcarbonyl, hydroxy-lower alkyl or cyano-lower alkyl; and $R^2$ represents a group selected from:

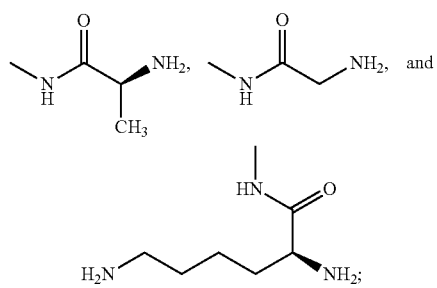

and pharmaceutically acceptable salts thereof.

The furazanobenzimidazoles of formula (II) are prodrugs with improved aqueous solubility and are cleaved in vivo to provide the corresponding parent drug of formula (I-II):

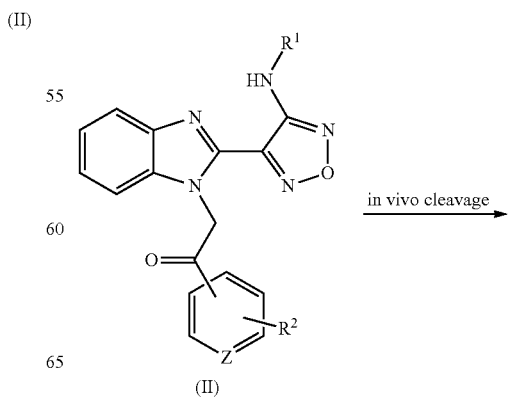

(II)

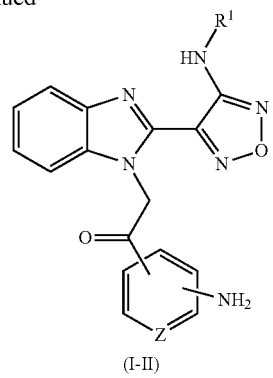

(I-II)

wherein R¹ and Z have the same meaning as in formula (II). The compounds are also cleaved in cellular assays and full blood.

The furazanobenzimidazoles of formula (II) have accordingly the same medicinal uses of the corresponding parent drugs which are described in detail in WO2004/103994. In particular, the compounds of formula (II) selectively induce apoptosis in cancer cells and can be used for the treatment of neoplastic and autoimmune diseases. The invention accordingly also relates to compounds of formula (II) for use as medicaments. The invention furthermore relates to methods for the synthesis of such compounds, to pharmaceutical compositions containing compounds of formula (II), to the use of compounds of formula (II) for the preparation of a pharmaceutical composition for the treatment of neoplastic and autoimmune diseases, and to methods of treatment of neoplastic and autoimmune diseases using such compounds of formula (II) or of pharmaceutical compositions containing the same.

For the purposes of the present application, the prefix "lower" denotes a radical having from 1 up to and including a maximum of 7, especially from 1 up to and including a maximum of 4 carbon atoms, the radicals in question being either linear or branched with single or multiple branching.

Where the plural form is used for compounds, salts, and the like, this is taken to mean also a single compound, salt, or the like.

Double bonds in principle can have E- or Z-configuration. The compounds of this invention may therefore exist as isomeric mixtures or single isomers. If not specified, both isomeric forms are intended.

Any asymmetric carbon atom not indicated in formula (II) to have a specific configuration may be present in the (R)-, (S)- or (R,S)-configuration, preferably in the (R)- or (S)-configuration. The compounds may thus be present as mixtures of isomers or as pure isomers, preferably as enantiomer-pure stereoisomers.

The invention relates also to possible tautomers of the compounds of formula (II).

Lower alkyl has preferably 1 to 4 carbon atoms and is butyl, such as n-butyl, sec-butyl, isobutyl, tert-butyl, propyl, such as n-propyl or isopropyl, ethyl or methyl. Preferably lower alkyl is methyl or ethyl.

Cycloalkyl has preferably 3 to 7 ring atoms, and may be unsubstituted or substituted, e.g. by lower alkyl or lower alkoxy. Cycloalkyl is, for example, cyclohexyl, cyclopentyl, or methylcyclopentyl.

Aryl stands for a mono- or bicyclic fused ring aromatic group with 5 to 10 carbon atoms, such as phenyl, 1-naphthyl or 2-naphthyl, or also a partially saturated bicyclic fused ring comprising a phenyl group, such as indanyl, dihydro- or tetrahydronaphthyl.

If

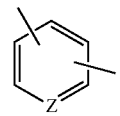

represents a divalent benzene residue and comprises further substituents these are preferably lower alkyl, lower alkoxy, lower alkoxy-lower alkoxy, amino, optionally substituted by one or two substituents selected from lower alkyl, lower alkenyl and alkylcarbonyl, methylenedioxy, halo-lower alkyl, lower alkoxy-lower alkyl or halogen, more preferably lower alkyl, lower alkoxy, lower alkoxy-lower alkoxy, methylenedioxy, halo-lower alkyl, lower alkoxy-lower alkyl or halogen.

The divalent benzene residue is preferably 1,4-phenylene.

Heteroaryl represents an aromatic group containing at least one heteroatom selected from nitrogen, oxygen and sulfur, and is mono- or bicyclic. Monocyclic heteroaryl includes 5 or 6 membered heteroaryl groups containing 1, 2, 3 or 4 heteroatoms selected from nitrogen, sulfur and oxygen. Bicyclic heteroaryl includes 9 or 10 membered fused-ring heteroaryl groups. Examples of heteroaryl include pyrrolyl, thienyl, furyl, pyrazolyl, imidazolyl, triazolyl, oxazolyl, isoxazolyl, oxadiazolyl, thiazolyl, isothiazolyl, thiadiazolyl, pyridyl, pyridazinyl, pyrimidinyl, pyrazinyl, benzo fused derivatives of such monocyclic heteroaryl groups, such as indolyl, benzimidazolyl or benzofuryl, quinolinyl, isoquinolinyl, quinazolinyl, or purinyl.

If

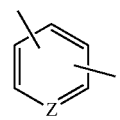

represents a divalent pyridine group and comprises further substituents these are preferably lower alkyl, lower alkoxy, lower alkoxy-lower alkoxy, amino, optionally substituted by one or two substituents selected from lower alkyl, lower alkenyl and alkylcarbonyl, halo-lower alkyl, lower alkoxy-lower alkyl, or halogen, more preferably lower alkoxy, amino or halogen.

Preferably, the divalent pyridine group is a group of formula

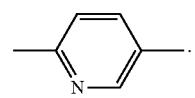

Heterocyclyl designates preferably a saturated, partially saturated or unsaturated, mono- or bicyclic ring containing 4-10 atoms comprising one, two or three heteroatoms selected from nitrogen, oxygen and sulfur, which may, unless otherwise specified, be carbon or nitrogen linked, wherein a ring nitrogen atom may optionally be substituted by a group selected from lower alkyl, amino-lower alkyl, aryl, aryl-lower alkyl and acyl, and a ring carbon atom may be substituted by lower alkyl, amino-lower alkyl, aryl, aryl-lower alkyl, heteroaryl, lower alkoxy, hydroxy or oxo. Examples of heterocyclyl are pyrrolidinyl, oxazolidinyl, thiazolidinyl, piperidinyl, morpholinyl, piperazinyl, dioxolanyl and tetrahydropyranyl.

Acyl designates, for example, lower-alkylcarbonyl, cyclohexylcarbonyl, arylcarbonyl, aryl lower alkylcarbonyl, or heteroarylcarbonyl. Acyl is preferably lower alkylcarbonyl, in particular propionyl or acetyl.

Hydroxy-lower alkyl is preferably hydroxymethyl, 2-hydroxyethyl or 2-hydroxy-2-propyl.

Cyano-lower alkyl designates preferably cyanomethyl and cyanoethyl.

Halo-lower alkyl is preferably fluoro-lower alkyl, especially trifluoromethyl, 3,3,3-trifluoroethyl or pentafluoroethyl.

Halogen is fluorine, chlorine, bromine, or iodine.

Lower alkoxy is especially methoxy, ethoxy, isopropyloxy, or tert-butyloxy.

Salts are especially the pharmaceutically acceptable salts. Such salts are formed, for example, as acid addition salts, preferably with organic or inorganic acids, from compounds of formula (II) with a basic nitrogen atom. Suitable inorganic acids are, for example, halogen acids, such as hydrochloric acid, sulfuric acid, or phosphoric acid. Suitable organic acids are, for example, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methyl-benzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula (II) can be used in the same way as the corresponding parent drugs. Therefore the invention also relates to compounds of formula (II) as defined hereinbefore for use as medicaments, in particular for the treatment of a neoplastic disease, autoimmune disease, transplantation related pathology and/or a degenerative disease, in particular for the treatment of a solid neoplastic disease.

The compounds of formula (II) according to the invention show therapeutic efficacy especially against neoplastic diseases and autoimmune diseases. In particular, the compounds of the invention are active against malignancies, e.g. epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas, Hodgkin's and non Hodgkin's lymphomas, other lymphoreticular neoplasms, plasma cell tumors, mast cell tumors, immunoproliferative diseases, leukemias, miscellaneous myeloproliferative disorders, lymphoproliferative disorders and myelodysplastic syndromes.

In particular, a compound of formula (II) according to the invention shows therapeutic efficacy especially against solid neoplastic diseases, e.g. epithelial neoplasms, squamous cell neoplasms, basal cell neoplasms, transitional cell papillomas and carcinomas, adenomas und adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas.

The compounds of the invention are likewise active against autoimmune diseases, e.g. against systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barré syndrome, dermatomyositis/polymyositis, autoimmune hemolytic anemia, thrompocytopenic purpura, neutropenia, type I diabetes mellitus, thyroiditis (including Hashimoto's and Grave' disease), Addison's disease, polyglandular syndrome, pemphigus (vulgaris, foliaceus, sebaceous and vegetans), bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia greata, primary biliary cirrhosis, autoimmune hepatitis, all forms of glomerulonephritis, pulmonal hemorrhage (goodpasture syndrome), IgA nephropathy, pernicious anemia and autoimmune gastritis, inflammatory bowel diseases (including colitis ulcerosa and morbus Crohn), Behcet's disease, Celic-Sprue disease, autoimmune uveitis, autoimmune myocarditis, granulomatous orchitis, aspermatogenesis without orchitis, idiopatic and secondary pulmonary fibrosis, inflammatory diseases with a possibility of autoimmune pathogensesis, such as pyoderma gangrensosum, lichen ruber, sarcoidosis (including Lofgren and cutaneous/subcutaneous type), granuloma anulare, allergic type I and type IV immunolgical reaction, asthma bronchiale, pollinosis, atopic, contact and airborne dermatitis, large vessel vasculitis (giant cell and Takayasu's arteritis), medium sized vessel vasculitis (polyarteritis nodosa, Kawasaki disease), small vessel vasculitis (Wegener's granulomatosis, Churg Strauss syndrome, microscopic polangiitis, Henoch-Schoenlein purpura, essential cryoglobulinemic vasculitis, cutaneous leukoldastic angiitis), hypersensitivity syndromes, toxic epidermal necrolysis (Stevens-Johnson syndrome, erythema multiforme), diseases due to drug side effects, all forms of cutaneous, organ-specific and systemic effects due to type I-VI (Coombs classification) immunologic forms of reaction, transplantation related pathologies, such as acute and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genito-urinary system, ear, cartilage, primary and secondary lymphatic system including bone marrow, lymph node, thymus, gastrointestinal tract, including oro-pharynx, esophageus, stomach, small intestine, colon, and rectum, including parts of above mentioned organs down to single cell level and substructures, e.g. stem cells).

A compound of formula (II) can be administered alone or in combination with one or more other therapeutic agents, possible combination therapy taking the form of fixed combinations, or the administration of a compound of the invention and one or more other therapeutic agents being staggered or given independently of one another, or the combined administration of fixed combinations and one or more other therapeutic agents. A compound of formula (II) can, besides or in addition, be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk. Particularly preferred is the use of compounds of formula (II) in combination with radiotherapy.

Therapeutic agents for possible combinations are especially one or more cytostatic or cytotoxic compounds, for example a chemotherapeutic agent or several selected from the group comprising indarubicin, cytarabine, interferon, hydroxyurea, bisulfan, or an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, an inhibitor of the interaction of an SH2 domain with a phosphorylated protein, an inhibitor of Bcl-2 and modulators of the Bcl-2 family members such as Bax, Bid, Bad, Bim, Nip3 and BH3-only proteins A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard to permit a comparison with other compounds.

BRIEF DESCRIPTION OF THE DRAWINGS

FIG. 1 shows a comparison of the anti-tumor activity of the lysine-prodrug according to Example 1 and the corresponding parent drug in SW480 colorectal cancer xenografts after once weekly intravenous application.

FIG. 2 shows a comparison of the anti-tumor activity of said compounds in SW480 colorectal cancer xenografts after 3 times weekly intravenous application.

With the groups of preferred compounds of formula (II) mentioned hereinafter, definitions of substituents from the general definitions mentioned hereinbefore may reasonably be used, for example, to replace more general definitions with more specific definitions or especially with definitions characterized as being preferred.

A specific embodiment of the invention are compounds of formula (II) as such, i.e. which are not in form of a salt. It has been found namely that the salt form is not required to provide a sufficient solubility of the compounds in aqueous media. This is particularly the case with the compound of formula (II) wherein $R^2$ represents the group of formula

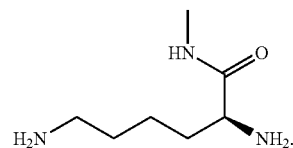

These compounds are already very well soluble in aqueous media having a pH between 6.5 and 5.

Preferred are the compounds of formula (II) wherein the group

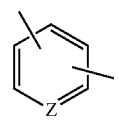

represents 1,4-phenylene or a group of formula

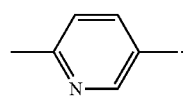

Another preferred group of the compounds of formula (II) are those wherein $R^1$ represents hydrogen or cyano-lower alkyl, in particular cyanoethyl.

A further especially preferred selection of the compounds of formula (II) are the compounds of formulae

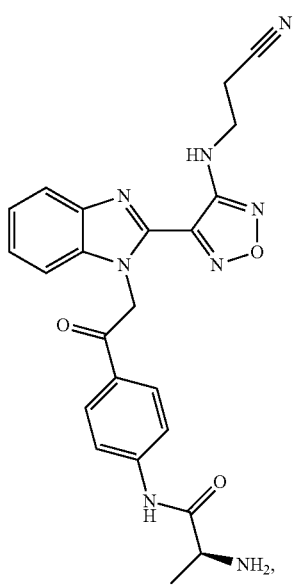
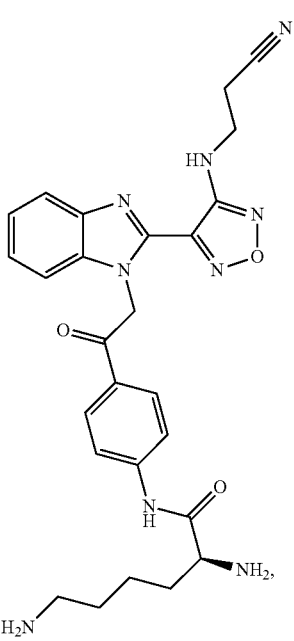
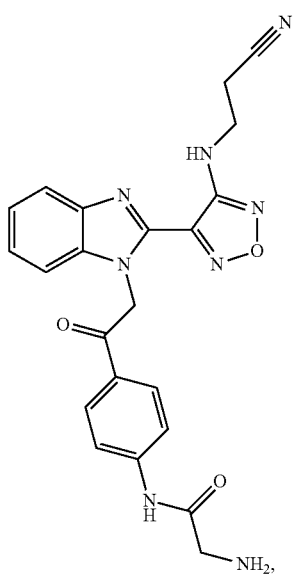
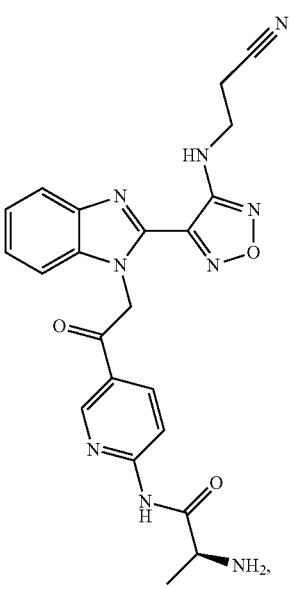

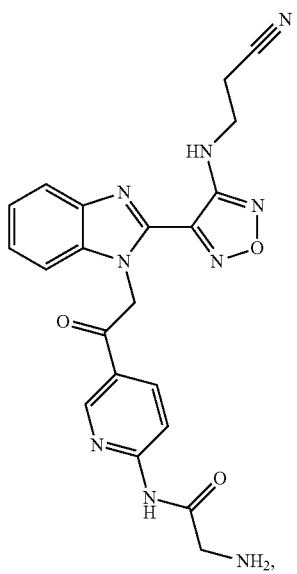
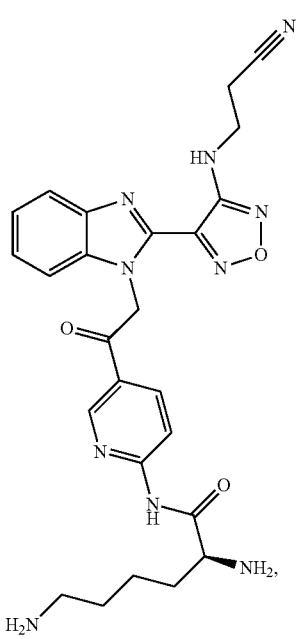 [SMILES: N#CCCNc1nonc1-c1nc2ccccc2n1CC(=O)c1ccc(NC(=O)[C@@H](N)CCCCN)cc1]
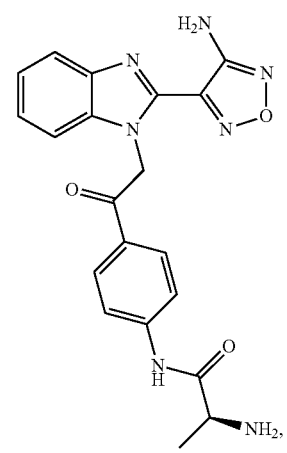
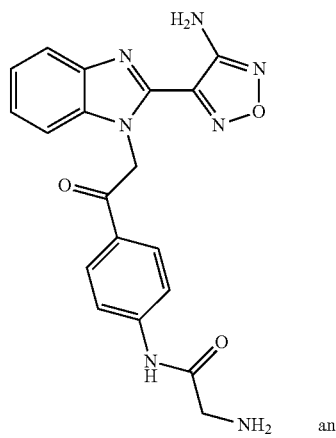
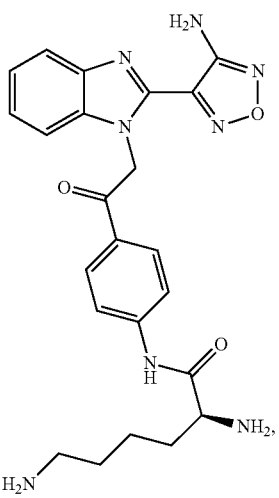
especially the compounds of formulae
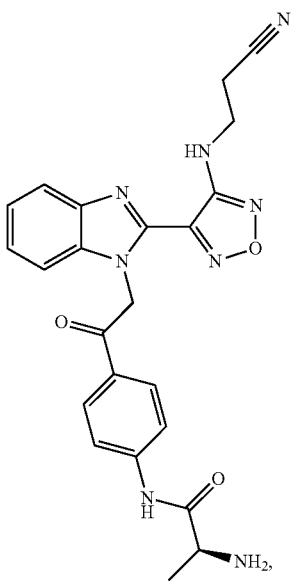

-continued

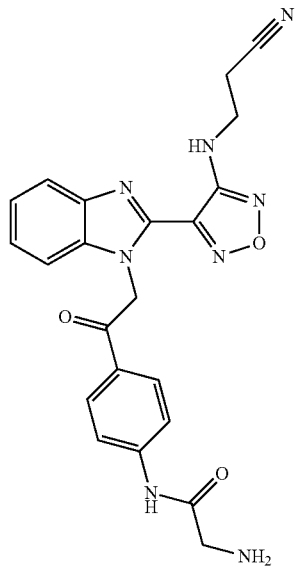

and

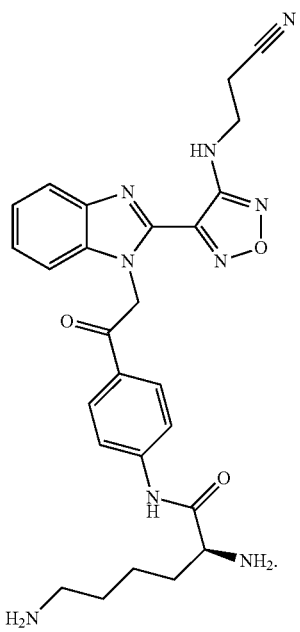

Most preferred is the compound having the formula

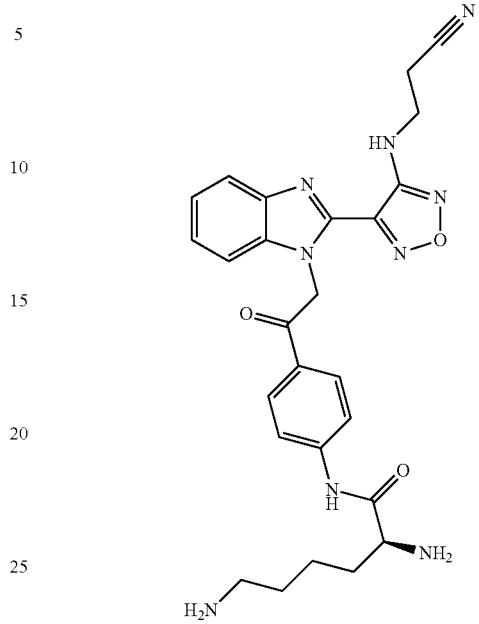

and pharmaceutically acceptable salts thereof, e.g. a hydrochloride salt.

The compounds of the invention may be prepared by processes that are known per se, in particular, a process, wherein a compound of formula (I-II)

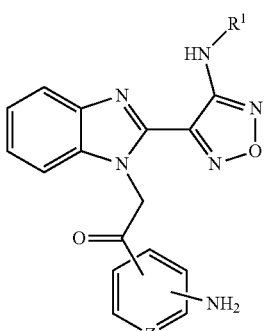

(I-II)

wherein $R^1$ and Z are defined as for formula (II) and wherein the group

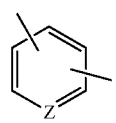

can optionally be further substituted by one or two additional substituents as defined above or a derivative of such a compound comprising functional groups in protected form, or a salt thereof is
(1) acylated with an amino acid of formula (III)

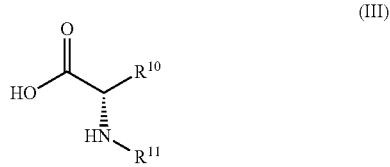

wherein $R^{10}$ is selected from hydrogen (Gly); methyl (Ala) and protected aminobutyl (Lys) and $R^{11}$ is a suitable amino protecting group, and (2) any protecting groups in a protected derivative of the resulting compound are removed to yield a compound of formula (II) and, if so desired, (3) said compound of formula (II) is converted into a salt as described above, or a salt of a compound of formula (II) is converted into the corresponding free compound of formula (II) or into another salt, and/or a mixture of isomeric product compounds is separated into the individual isomers.

Acylation of a compound of formula (I-II) with an amino acid of formula (III) is performed in a manner known per se, usually in the presence of a suitable polar or dipolar aprotic solvent, with cooling or heating as required, for example in a temperature range from approximately minus 80° C. to approximately plus 150° C., more preferably from minus 30° C. to plus 120° C., especially in a range from approximately around 0° C. to the reflux temperature of the used solvent. Optionally a suitable base is added, in particularly an aromatic base like pyridine or collidine or a tertiary amine base such as triethylamine or diisopropylethylamine, or an inorganic basic salt, e.g. potassium or sodium carbonate.

Acylation may be accomplished under conditions used for amide formation known per se in peptide chemistry, e.g. with activating agents for the carboxy group, such as carbodiimides like N,N'-diethyl-, N,N'-dipropyl-, N,N'-diisopropyl-, N,N'-dicyclohexylcarbodiimide and N-(3-dimethylaminoisopropyl)-N'-ethylcarbodiimide-hydrochloride (EDC), or with agents such as 1-hydroxybenzotriazole (HOBt), benzotriazol-1-yloxytris(dimethylamino)-phosphonium hexafluorophosphate (BOP), O-(7-aza-benzotriazol-1-yl)-N,N,N',N'-tetramethyl-uronium hexafluorophosphate (HATU), 2-(2-oxo-1-(2H)-pyridyl)-1,1,3,3-tetramethyluronium tetrafluoroborate (TPTU), optionally in the presence of suitable bases, catalysts or co-reagents. The carboxy group may also be activated as acyl halogenide, preferably as acyl chloride, e.g. by reaction with thionylchloride or oxalylchloride, or as symmetrical or unsymmetrical anhydride, e.g. by reaction with halogeno formates like ethyl chloroformate, optionally in the presence of suitable bases, catalysts or co-reagents.

If one or more other functional groups, for example carboxy, hydroxy or amino, are or need to be protected in a compound of formula (I-II) or (III), because they should not take part in the reaction, these are such protecting groups as are usually applied in the synthesis of amides like, in particular peptide compounds, cephalosporins, penicillins, nucleic acid derivatives and sugars, which are known to the skilled persons. Suitable protecting groups for amino groups are for example t-butyl carbamate, benzyl carbamate or 9-fluorenylmethyl carbamate.

The protecting groups may already be present in precursors and should protect the functional groups concerned against unwanted secondary reactions, such as alkylation, acylation, etherification, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis and in special books on protective groups such as J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, G. M. Wuts "Protective Groups in Organic Synthesis", Wiley, New York, 2006.

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of formula (II) with a salt-forming group may be prepared in a manner known per se. Acid addition salts of compounds of formula (II) may thus be obtained by treatment with an acid or with a suitable anion exchange reagent.

Salts can usually be converted to free compounds, e.g. for acid addition salts by treating with suitable basic agents, for example with alkali metal carbonates, alkali metal hydrogencarbonates, or alkali metal hydroxides, typically potassium carbonate or sodium hydroxide.

It should be emphasized that reactions analogous to the conversions mentioned in this chapter may also take place at the level of appropriate intermediates.

All process steps described here can be carried out under known reaction conditions, preferably under those specifically mentioned, in the absence of or usually in the presence of solvents or diluents, preferably such that are inert to the reagents used and able to dissolve these, in the absence or presence of catalysts, condensing agents or neutralising agents, for example ion exchangers, typically cation exchangers, for example in the H$^+$ form, depending on the type of reaction and/or reactants at reduced, normal, or elevated temperature, for example in the range from (minus 100)° C. to about 190° C., preferably from about (minus 80)° C. to about 150° C., for example at (minus 80) to 60° C., at (minus 20) to 40° C., at room temperature, or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures.

In the preferred embodiment, the compounds of formula (II) are prepared according to or in analogy to the processes and process steps described in the Examples.

The compounds of formula (II), including their salts, can also be in the form of hydrates or solvates.

The starting materials of formula (I-II) and (III) are known and are either commercially available or can be synthesized in analogy to or according to methods that are known in the art. The manufacture of compounds of formula (I-II) is e.g. described in WO2004/103994 and can be performed e.g. according to the following general reaction scheme:

19
20
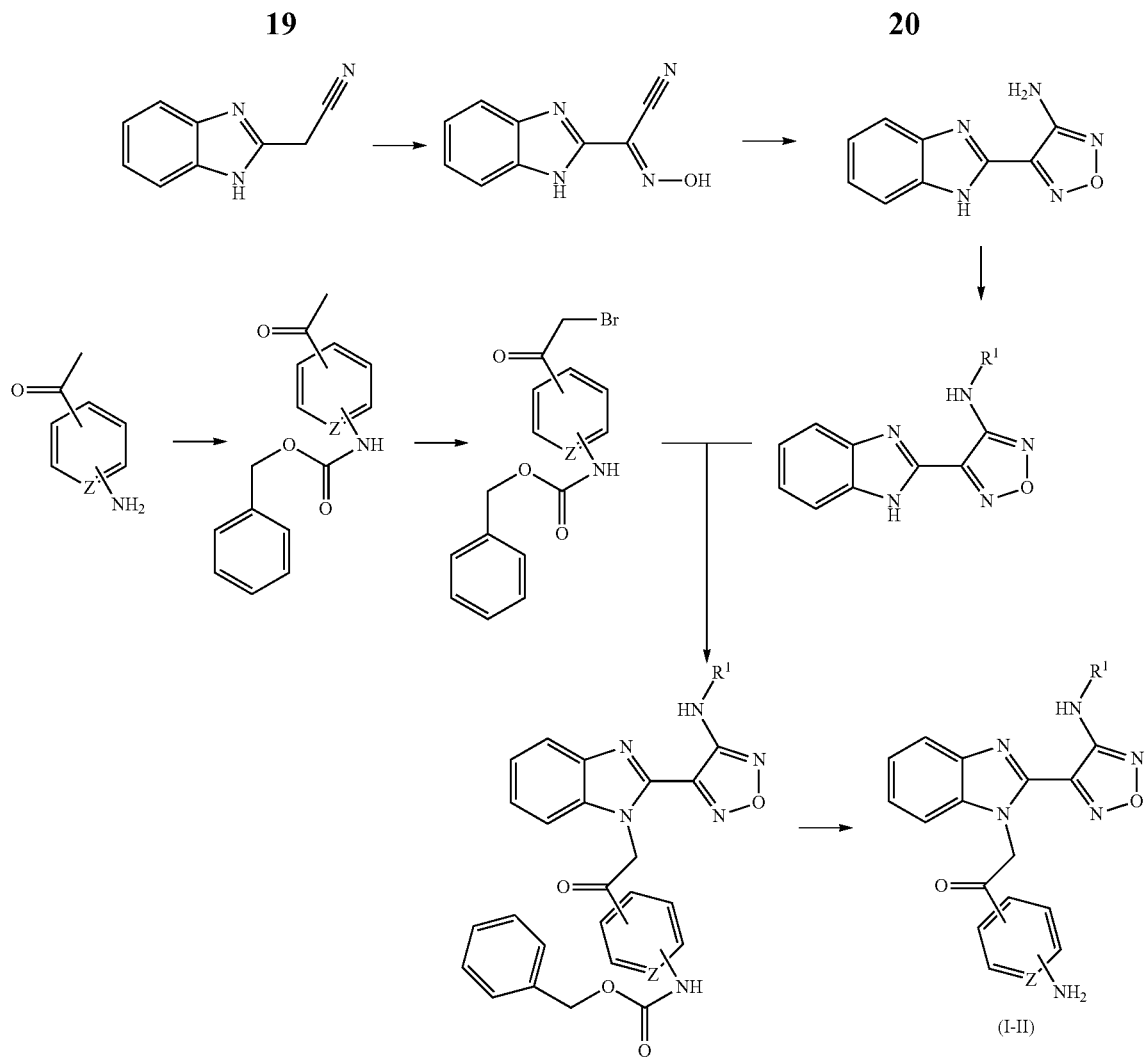
The compounds of formula (II) can also be manufactured as shown for the corresponding lysine amide prodrugs in the following reaction scheme, wherein "Cbz" means benzyloxycarbonyl:
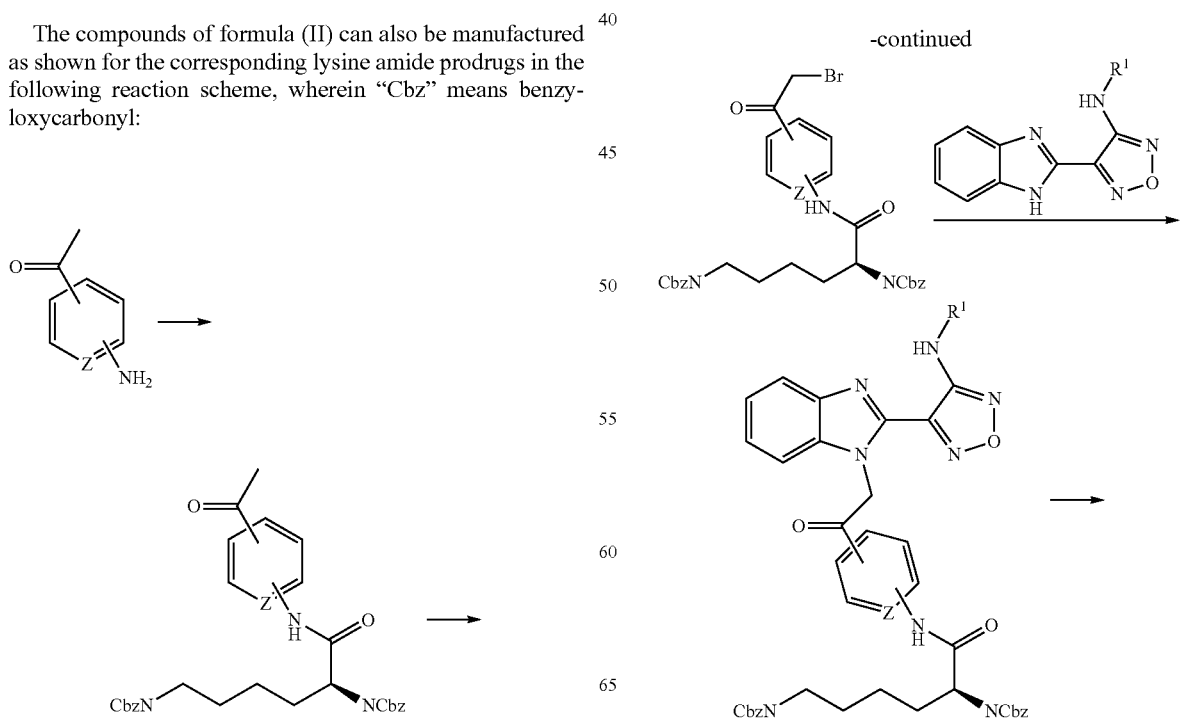

-continued

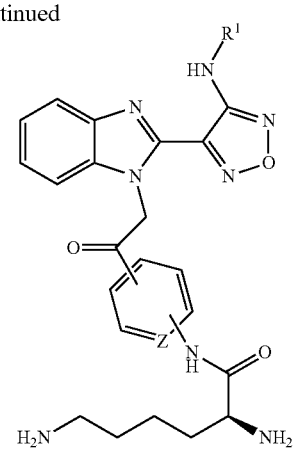

This process cannot only be used for manufacturing the compounds of present formula (II) but can advantageously also be used for manufacturing prodrug amides of compounds of formula (I) as defined in WO2004/103994 with any naturally occurring amino acid in general, e.g the prodrug amides of the compounds of formula (I-II) as defined above with said amino acids, i.e. with glycine, alanine, arginine, asparagine, asparaginic acid, cysteine, glutamine, glutaminic acid, histidine, isoleucine, leucine, lysine, methonine, phenylalanine, proline, serine, threonine, tryptophane, tyrosine or valine for example.

The invention therefore also relates to a process for the manufacture of a compound of formula (II-G):

(II-G)

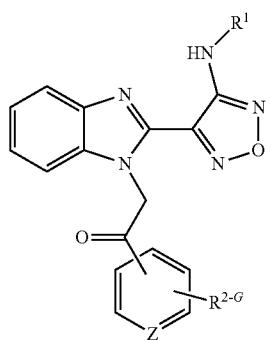

or a salt thereof,
comprising the steps:
(a) reacting a compound of formula

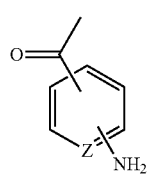

with an alpha-amino acid derivative of the formula:

in the presence of an activating agent and optionally in the presence of suitable bases, catalysts or co-reagents, preferably in the presence of O-(7-azabenzotriazol-1-yl)-N,N,N′,N′-tetramethyluronium hexafluorophosphate (HATU) and 2,4,6-collidine to yield the compound of formula:

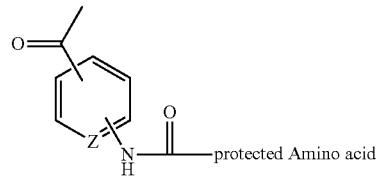

(b) reacting the product of Step (a) with a bromination agent like bromine or cupric bromide, preferably cupric bromide to yield the bromo compound of formula:

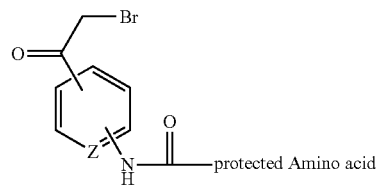

(c) reacting said bromo compound obtained in Step (b) with a compound of formula:

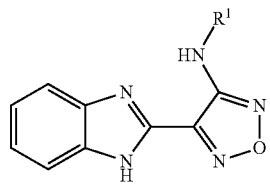

in the presence of a base, e.g. potassium carbonate, to yield the compound of formula:

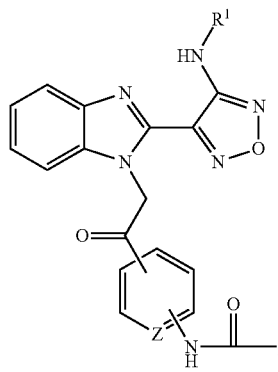

(d) removing any protection groups being present from the group "protected Amino acid" to yield the compound of formula (II-G) and, optionally,
(e) converting said compound of formula (II-G) to a salt thereof,
in which formulae $R^1$ and

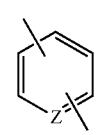

have one of the meanings described hereinabove, $R^{2-G}$ is a group of formula

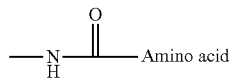

"Amino acid" represents a residue derived from a natural alpha-amino acid by removing the carboxyl group from the alpha-carbon atom of said amino acid, and "protected Amino acid" means the same amino acid as "Amino acid", primary amino groups and if required also other functional groups of said amino acid however being protected by a suitable protecting group. Suitable protective groups are known to those skilled in the art and are e.g. described in "Protective Groups in Organic Synthesis." Third Edition By Theodora W. Greene and Peter G. M. Wuts. John Wiley & Sons, New York. 1999. xxi+779 pp. 16×24 cm. ISBN 0-471-16019-9

The present invention relates also to pharmaceutical compositions that comprise a compound of formula (II) as active component or ingredient and that can be used especially as a medicament, in particular in the treatment of the diseases mentioned above.

Compositions for enteral administration, such as nasal, buccal, rectal or, especially, oral administration, or for parenteral administration, such as intravenous, intramuscular or subcutaneous administration, to warm-blooded animals, especially humans, are especially preferred. The compositions comprise the active ingredient, preferably together with a pharmaceutically acceptable carrier. The dosage of the active ingredient depends upon the disease to be treated and upon the species, its age, weight, and individual condition, the individual pharmacokinetic data, and the mode of administration.

The invention relates also to pharmaceutical compositions for use in a method for the prophylactic or especially therapeutic management of the human or animal body, in particular in a method of treating neoplastic disease, autoimmune disease, transplantation related pathology and/or degenerative disease, especially those mentioned hereinabove.

The invention relates also to processes and to the use of compounds of formula (II) for the preparation of pharmaceutical preparations which comprise compounds of formula (II) or salts thereof as a pharmaceutically active component.

The present invention also relates to the use of compounds of formula (II) in depot systems for local drug delivery such as biodegradable polymers.

A pharmaceutical composition for the prophylactic or especially therapeutic management of a neoplastic disease, autoimmune disease, transplantation related pathology and/or degenerative disease, of a warm-blooded animal, especially a human or a mammal requiring such treatment, comprising a compound of formula (II) as active ingredient in a quantity that is prophylactically or especially therapeutically active against the said diseases, is likewise preferred.

The pharmaceutical compositions comprise from approximately 1% to approximately 95% active ingredient. Single-dose administration forms preferably comprise from approximately 20% to approximately 90% active ingredient and forms that are not of single-dose type preferably comprise from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lip-sticks, drops, sprays, dispersions, etc. Examples are capsules containing from about 0.01 g to about 1.0 g active ingredient.

The pharmaceutical compositions of the present invention are prepared in a manner known per se, for example by means of conventional mixing, granulating, coating, dissolving or lyophilizing processes.

Specific preference is given to the use of solutions of the active ingredient, especially aqueous solutions, in particular isotonic aqueous solutions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The present invention relates furthermore to a method for the treatment of a neoplastic disease, autoimmune disease, transplantation related pathology and/or degenerative disease, which comprises administering a compound of formula (II) or a pharmaceutically acceptable salt thereof, wherein the radicals and symbols have the meanings as defined above for formula (II), in a quantity effective against said disease, to a warm-blooded animal requiring such treatment. The compounds of formula (II) can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.01 g to approximately 5 g, preferably from approximately 0.05 g to approximately 1.5 g, of a compound of the present invention.

The present invention relates especially also to the use of a compound of formula (II), or a pharmaceutically acceptable salt thereof, especially a compound of formula (II) which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, in particular a neoplastic disease, autoimmune disease, transplantation related pathology and/or degenerative disease.

The preferred dose quantity, composition, and preparation of pharmaceutical formulations (medicines) which are to be used in each case are described above.

The following Examples serve to illustrate the invention without limiting the invention in its scope.

EXAMPLES

Abbreviations: Cbz=benzyloxycarbonyl, DIPEA=N,N-di-isopropyl-N-ethylamine, DMAP=N,N-dimethylaminopyridine, DMF=N,N-dimethylformamide, DMSO=dimethyl sulfoxide, eq=equivalent, ESI=electrospray ionization, HATU=O-(7-azabenzotriazol-1-yl)-N,N,N',N'-tetramethyluronium hexafluorophosphate, THF=tetrahydrofuran.

All reagents and solvents are of commercial quality and used without further purification unless otherwise noted.

Reported temperatures are external bath temperatures unless otherwise noted.

Mass spectra (ESI-MS) are recorded on a Waters Micromass ZQ spectrometer, a Varian 1200L Quadrupole MS spectrometer or an Agileant 1100 LC/MSD spectrometer.

NMR spectra are obtained with a Broker Avance 400 MHz spectrometer or a Varian Mercury Plus 400 MHz spectrometer using DMSO-$d_6$, CDCl$_3$, acetone-$d_6$, CD$_3$OD, D$_2$O as solvent. The chemical shifts (δ) are expressed in ppm.

Example 1

(A) Synthesis of 3-(4-{1-[2-(4-amino-phenyl)-2-oxo-ethyl]-1H-benzoimidazol-2-yl}furazan-3-ylamino)-propionitrile

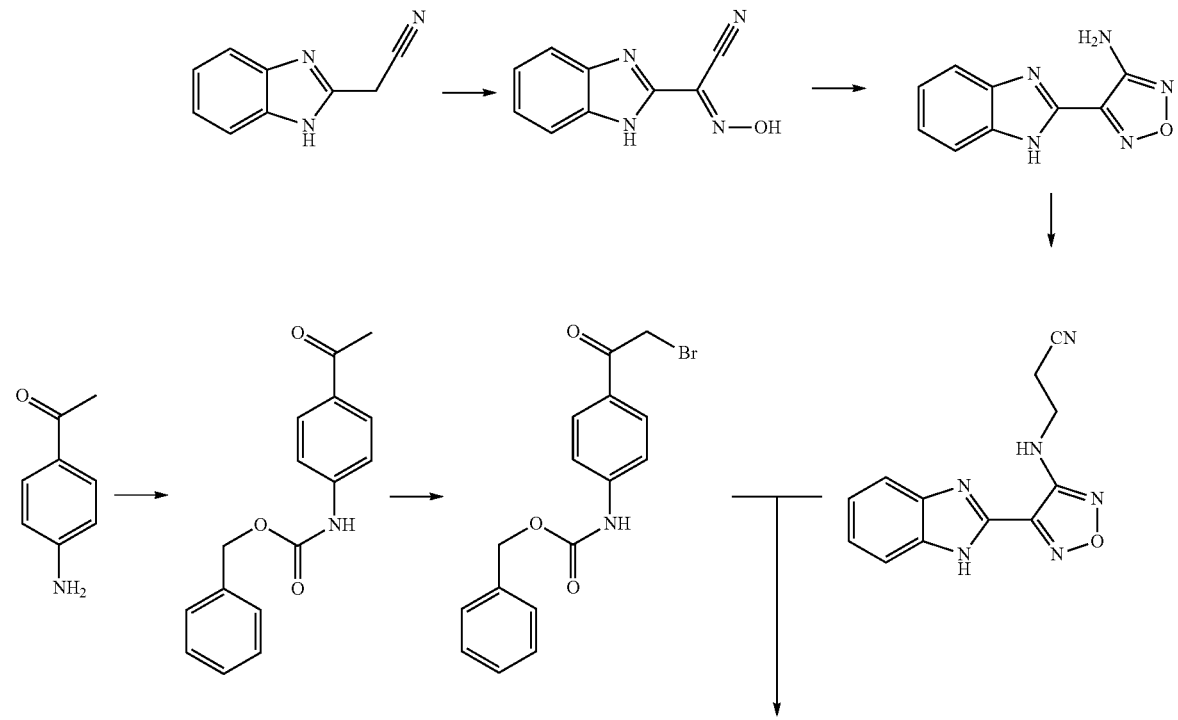

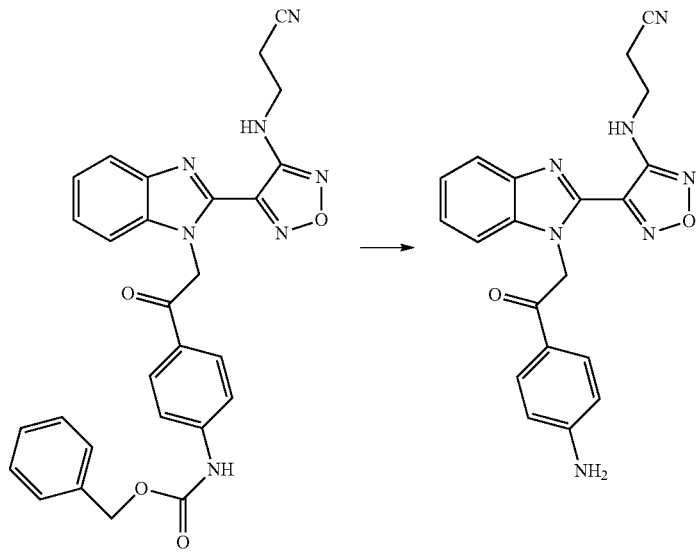

(4-Acetyl-phenyl)-carbamic acid benzyl ester

[4-(2-Bromo-acetyl)-phenyl]-carbamic acid benzyl ester

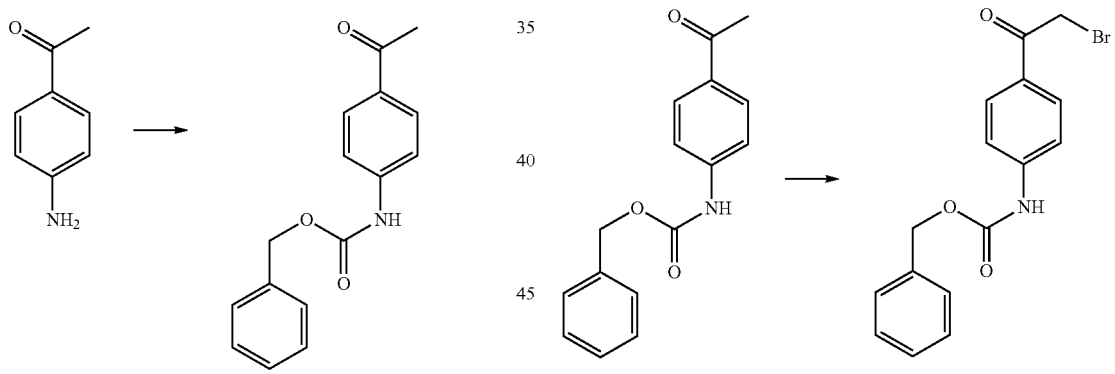

To a stirred solution of 10 g of 4-aminoacetophenone (74 mmol, 1 eq) in a mixture of 60 ml of water and 100 ml of dioxane at 0° C., 12.43 g of NaHCO$_3$ (148 mmol, 2 eq) and 15.3 g of benzyl chloroformate (85 mmol, 1.15 eq, purity 95%) are added. The mixture is stirred at room temperature for 4 h and then concentrated under reduced pressure to remove the dioxane. The suspension is diluted with 70 ml of water and 150 ml of ethyl acetate. The phases are separated and the organic layer is washed with 2×50 ml of brine, dried over Na$_2$SO$_4$, filtered and concentrated under reduced pressure to give 19.5 g of the product as solid.

MS (ESI+): 270 [M+H].

$^1$H NMR (400 MHz, DMSO-d$_6$) ppm: 10.18 (s, 1H), 7.92-7.89 (m, 2H), 7.61-7.58 (m, 2H), 7.46-7.33 (m, 5H), 5.18 (s, 2H), 2.51 (s, 3H).

A mixture of 18.5 g of (4-acetyl-phenyl)-carbamic acid benzyl ester (95%, 65.3 mmol, 1 eq) and 30.7 g of CuBr$_2$ (138 mmol, 2.1 eq) in 740 ml of ethanol is heated to reflux for 2 h. After cooling to room temperature, the mixture is filtered and the residue is washed with 2000 ml of ethyl acetate. The acidic (pH<1) combined filtrates of ethanol and ethyl acetate are brought to pH 5 by addition of aqueous 1 N NaOH solution. Then 200 ml of water are added. The organic phase is separated, washed with 3×200 ml of brine, dried over Na$_2$SO$_4$, filtered and concentrated under reduced pressure to give 23.78 g of the crude product as a solid, which is used in the next step without further purification.

MS (ESI+): 348+350 [M+H].

$^1$H NMR (400 MHz, DMSO-d$_6$) ppm: 10.26 (s, 1H), 8.00-7.90 (m, 2H), 7.65-7.59 (m, 2H), 7.46-7.34 (m, 5H), 5.19 (s, 2H), 4.84 (s, 2H).

(1H-Benzoimidazol-2-yl)-hydroxyimino-acetonitrile

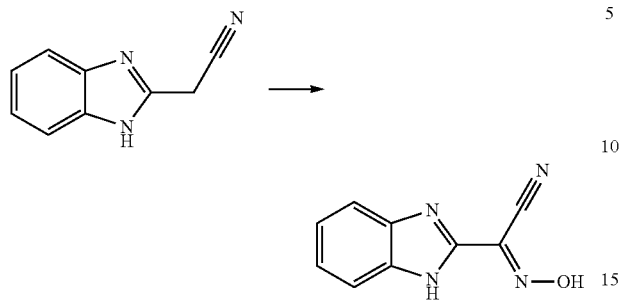

To an ice-cooled stirred solution of 10 g of 2-benzimidazolylacetonitrile (63.6 mmol, 1 eq) in 50 ml of glacial acetic acid is added dropwise a solution of 4.83 g of sodium nitrite (70 mmol, 1.1 eq) dissolved in a minimum amount of water (10 mL). When the addition is completed, the reaction mixture is allowed to stir at room temperature for 1 h. The precipitate formed in the course of the reaction is filtered and washed with 2×20 ml of cold water and 2×30 ml of diethylether to provide 11.8 g of the product as light yellow solid.

MS (ESI+): 187 [M+H].

$^1$H NMR (400 MHz, DMSO-$d_6$) ppm: 14.44 (broad, 1H), 13.15 (s, 1H), 7.80-7.20 (m, 4H).

4-(1H-Benzoimidazol-2-yl)-furazan-3-ylamine

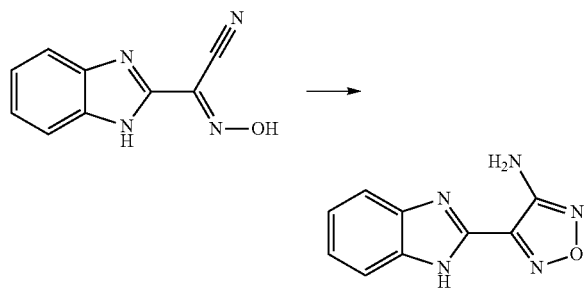

To an ice-cooled stirred solution of 13.2 g of hydroxylamine hydrochloride (190 mmol, 3 eq) in 20 ml of water, 15.3 g of potassium hydroxide (27.2 mmol, 4.3 eq) are slowly added. Then 60 ml of diglyme (diethylene glycol dimethyl ether) and 11.8 g of (1H-benzoimidazol-2-yl)-hydroxyimino-acetonitrile (63.4 mmol, 1 eq) are added. The ice-bath is removed and the reaction mixture is heated to reflux for 8 h (bath temperature 170° C.). After cooling to room temperature, the reaction mixture is filtered and the residue is washed with water to give the first crop of the desired product (6.2 g). The filtrate is treated with 150 ml of water. The resulting suspension is filtered and washed with water to provide a second product crop (2.17 g). Both crops are combined and used in the next step.

MS (ESI+): 202 [M+H].

$^1$H NMR (400 MHz, DMSO-$d_6$) ppm: 13.7 (broad, 1H), 7.78 (broad, 2H), 7.35-7.32 (m, 2H), 6.84 (s, 2H).

3-[4-(1H-Benzoimidazol-2-yl)-furazan-3-ylamino]-propionitrile

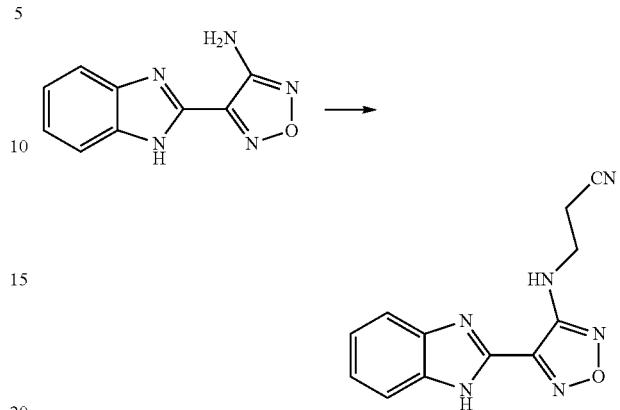

To an ice-cooled, stirred solution of 18.2 g of 4-(1H-benzoimidazol-2-yl)-furazan-3-ylamine (90.5 mmol, 1 eq) in 240 ml of pyridine are added 30 ml of sodium methoxide solution (30% in MeOH) (163 mmol, 1.8 eq) and subsequently 6 ml of acrylonitrile (90.5 mmol, 1 eq). The reaction mixture is stirred at room temperature overnight, before it is concentrated under reduced pressure. The residue is suspended in 250 ml of water and extracted with 4×400 ml of ethyl acetate. The combined organic layers are washed with 2×500 ml of brine, dried over $Na_2SO_4$, filtered and concentrated under reduced pressure. The crude product is dissolved in about 1000 ml of refluxing ethyl acetate. Then 1700 ml of n-hexane are added to the solution. The resulting turbid mixture is allowed to stand at room temperature overnight and the formed precipitate is filtered to provide 11.1 g of the product as light yellow solid. The filtrate is concentrated to dryness under reduced pressure and the residue is suspended in 100 ml of a 1/1 mixture of n-hexane/ethyl acetate. The suspension is filtered to provide 4.7 g additional product.

MS (ESI+): 255 [M+H].

$^1$H NMR (400 MHz, DMSO-$d_6$) ppm: 13.75 (broad, 1H), 7.81 (broad, 1H), 7.61 (broad, 1H), 7.37-7.34 (m, 2H), 7.21 (t, 1H, J=6 Hz), 3.68 (q, 2H, J=6 Hz), 2.94 (t, 2H, J=6 Hz).

[4-(2-{2-[4-(2-Cyano-ethylamino)-furazan-3-yl]-benzoimidazol-1-yl}-acetyl)-phenyl]-carbamic acid benzyl ester

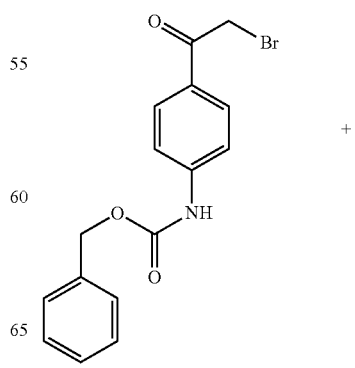

+

31

-continued

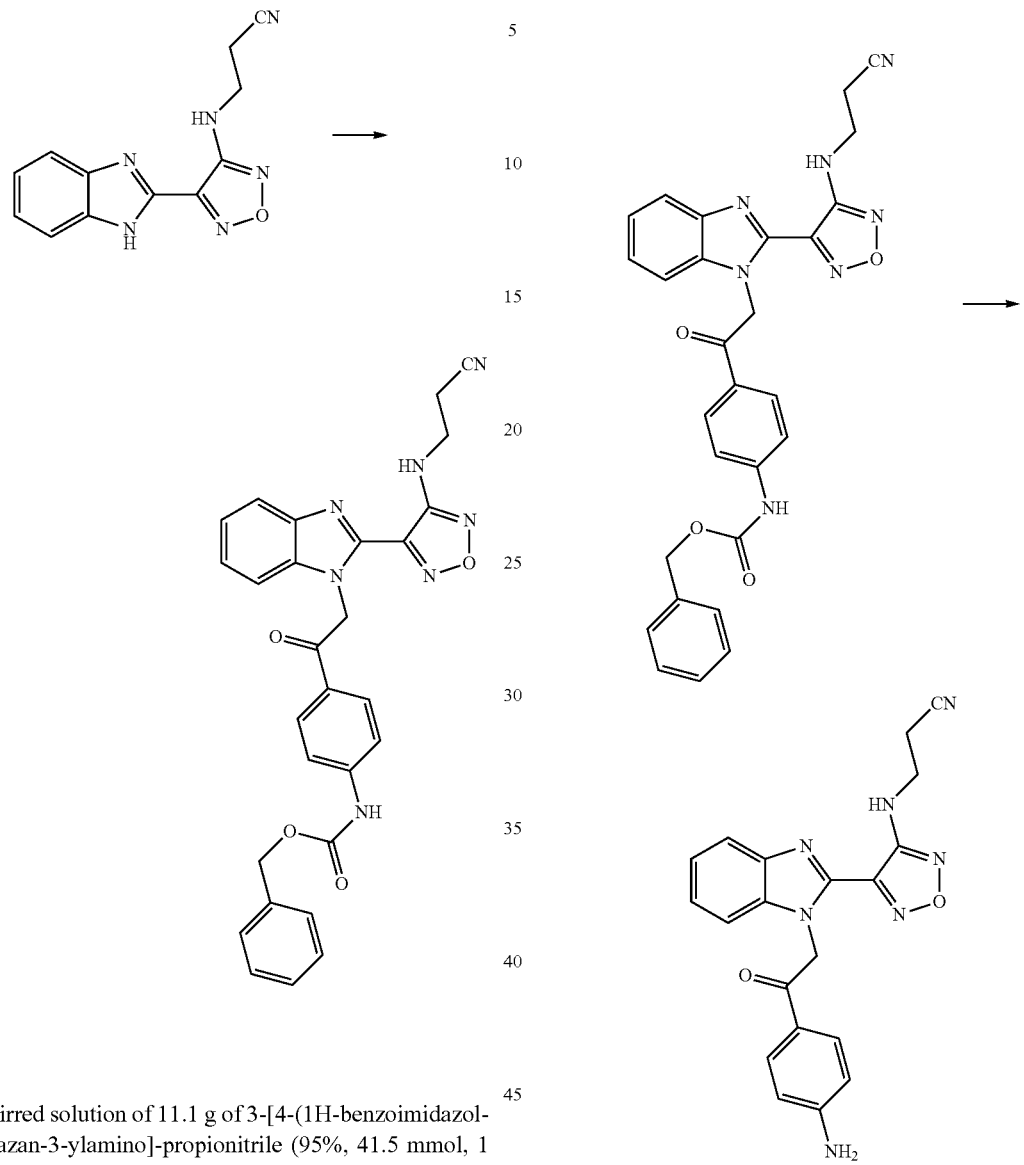

32
3-(4-{1-[2-(4-Amino-phenyl)-2-oxo-ethyl]-1H-benzoimidazol-2-yl}-furazan-3-ylamino)-propionitrile To a stirred solution of 11.1 g of 3-[4-(1H-benzoimidazol-2-yl)-furazan-3-ylamino]-propionitrile (95%, 41.5 mmol, 1 eq) in 90 ml of N,N-dimethylformamide are added 7.84 g of potassium carbonate (56.8 mmol, 1.3 eq), followed by 23.25 g of [4-(2-bromo-acetyl)-phenyl]-carbamic acid benzyl ester (75%, 50.1 mmol, 1.2 eq). The reaction mixture is stirred for 4 h at room temperature. Then 700 ml of water are added and the resulting suspension is extracted with 3×800 ml of ethyl acetate. The combined organic layers are washed with water and brine, dried over $Na_2SO_4$, filtered and concentrated to give the crude product as dark brown solid. This crude product is suspended in 150 ml of a 2/1 ethyl acetate/methanol mixture. Filtration provides 12.63 g of the desired product as light brown powder.

MS (ESI+): 522 [M+H].

$^1$H NMR (400 MHz, DMSO-$d_6$) ppm: 10.33 (s, 1H), 8.09 (d, 2H, J=9 Hz), 7.91-7.82 (m, 2H), 7.71 (d, 2H, J=9 Hz), 7.50-7.36 (m, 8H), 6.33 (s, 2H), 5.22 (s, 2H), 3.70-3.65 (m, 2H), 2.95 (t, 2H, J=6.5 Hz).

To a suspension of 6.4 g of [4-(2-{2-[4-(2-cyano-ethylamino)-furazan-3-yl]-benzoimidazol-1-yl}-acetyl)-phenyl]-carbamic acid benzyl ester (12.3 mmol, 1 eq) in a mixture of 700 ml of ethyl acetate and 500 ml of methanol are added 1.3 g of 10% palladium on carbon. The reaction mixture is stirred for 3 h under hydrogen atmosphere (1 atm) at room temperature. Then it is filtered through celite and concentrated under reduced pressure to give the crude product as a light yellow solid, which is suspended in 60 ml of a 7/5 ethyl acetate/methanol mixture. Filtration provides 3.5 g of the desired product as off-white solid. The filtrate is concentrated and the residue is treated as above with 5 ml of the 7/5 ethyl acetate/methanol mixture. Filtration gives 0.45 g of a second crop of the product.

MS (ESI+): 388 [M+H].

33
$^1$H NMR (400 MHz, DMSO-$d_6$) ppm: 7.89-7.87 (m, 1H), 7.83-7.77 (m, 3H), 7.47 (t, 1H, J=6 Hz), 7.42-7.38 (m, 2H), 6.67-6.65 (m, 2H), 6.28 (s, 2H), 6.19 (s, 2H), 3.70-3.66 (m, 2H), 2.95 (t, 2H, J=6.5 Hz).
(B) Preparation of S-2,6-diamino-hexanoic acid [4-(2-{2-[4-(2-cyano-ethylamino)-furazan-3-yl]-benzoimidazol-1-yl}-acetyl)-phenyl]-amide
Procedure I
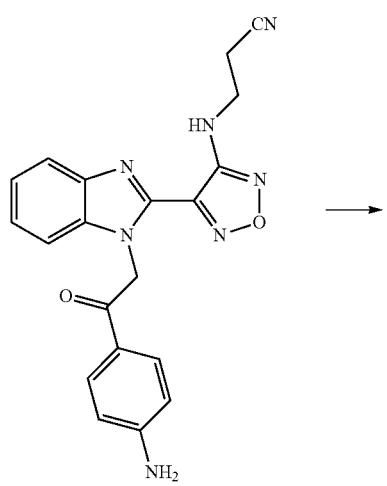
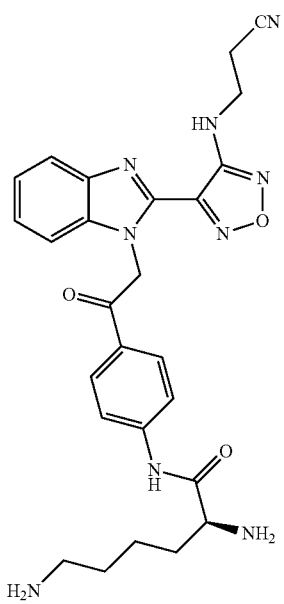
S-{5-benzyloxycarbonylamino-5-[4-(2-{2-[4-(2-cyano-ethylamino)-furazan-3-yl]-benzoimidazol-1-yl}-acetyl)-phenylcarbamoyl]-pentyl}-carbamic acid benzylester
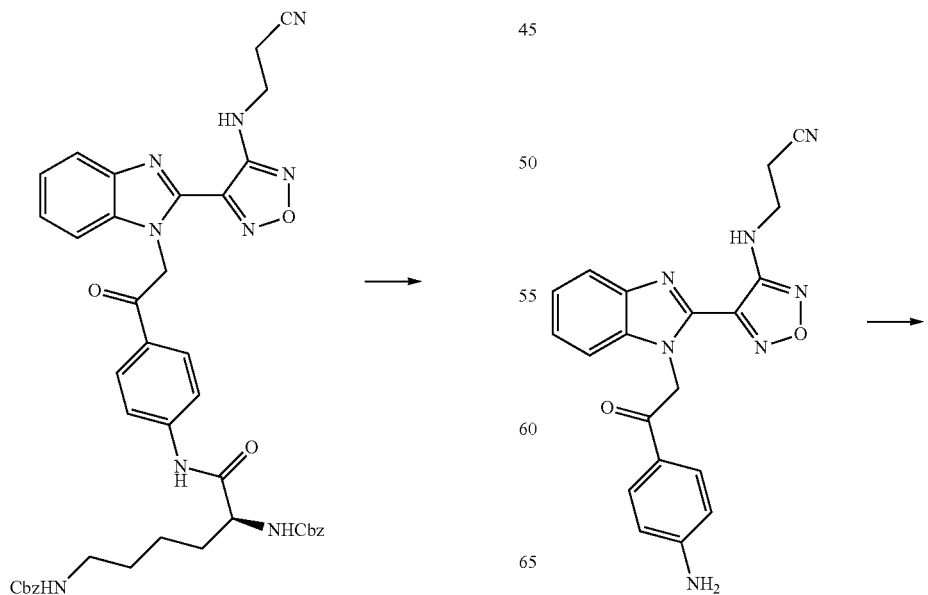

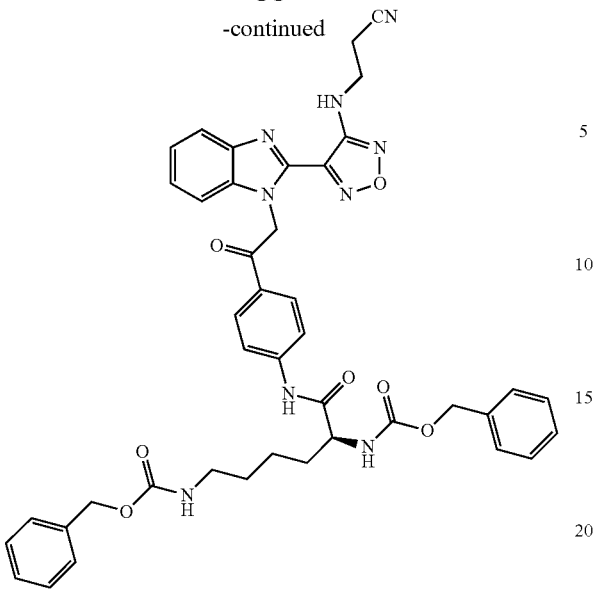

Method A

To a solution of 1.926 g N,N-di-Z-L-lysine (4.65 mmol; 1.2 eq) in 10 ml dry N,N-dimethylformamide at 0° C. are added 0.862 g of 4-methylmorpholine (8.52 mmol; 0.937 ml; 2.2 eq) and 0.572 g of ethyl chloroformate (5.27 mmol; 0.503 ml; 1.36 eq) and the mixture is stirred at 0° C. for 10 min. Then a solution of 1.5 g of 3-(4-{1-[2-(4-amino-phenyl)-2-oxo-ethyl]-1H-benzoimidazol-2-yl}-furazan-3-ylamino)-propionitrile (3.87 mmol; 1 eq) in 10 ml dry N,N-dimethylformamide is added and the mixture is stirred at room temperature overnight. The conversion is not complete, therefore another 0.385 g of N,N-di-Z-L-lysine (0.93 mmol; 0.24 eq) in a small amount of N,N-dimethylformamide and 0.172 g of 4-methylmorpholine (1.7 mmol; 0.187 ml; 0.44 eq) and 0.114 g of ethyl chloroformate (1.05 mmol; 0.1 ml; 0.27 eq) are added and the reaction mixture is stirred overnight at room temperature. Then the reaction mixture is diluted with ethyl acetate and washed with 5% citric acid solution and brine. The organic layer is dried over magnesium sulfate, filtered and concentrated under reduced pressure. The residue is washed with a mixture of dichloromethane and diisopropylether and dried under reduced pressure to provide 2.38 g of the product as an off-white solid.

MS (ESI+): 784.5 [M+H].

$^1$H-NMR (DMSO-$d_6$) ppm: 10.5 (s, 1H), 8.12 (d, J=8.8 Hz, 2H), 7.91-7.84 (m, 4H), 7.66 (d, J=7.5 Hz, 1H), 7.48-7.26 (m, 14H), 6.35 (s, 2H), 5.06 (s, 2H), 5.00 (s, 2H), 4.21-4.15 (m, 1H), 3.69 (q, J=6.5 Hz, 2H), 3.01-2.94 (m, 4H), 1.80-1.65 (m, 2H), 1.50-1.25 (m, 4H).

Method B 3.73 g of N,N-di-Z-L-lysine (9.0 mmol; 1.2 eq), 1.82 g of 2,3,5-collidine (15 mmol; 1.95 ml; 2 eq) and 5.7 g of HATU (15 mmol; 2 eq) are dissolved in 50 ml of dry N,N-dimethylformamide and the mixture is stirred at room temperature for 5 min. Then a solution of 2.9 g of 3-(4-{1-[2-(4-amino-phenyl)-2-oxo-ethyl]-1H-benzoimidazol-2-yl}-furazan-3-ylamino)-propionitrile (7.5 mmol; 1 eq) in 30 ml dry N,N-dimethylformamide is added and the mixture is stirred at room temperature for 2 days. Another 0.37 g of N,N-di-Z-L-lysine (0.9 mmol; 0.12 eq) are added and the mixture is stirred for one day at room temperature. Another 0.74 g of N,N-di-Z-L-lysine (1.8 mmol; 0.24 eq), 0.36 g of 2,3,5-collidine (3 mmol; 0.39 ml; 0.4 eq) and 1.14 g of HATU (3 mmol; 0.4 eq) are added and the reaction mixture is stirred for one day at room temperature.

Then the reaction mixture is diluted with ethyl acetate and washed with water, 5% citric acid solution and brine. The organic layer is dried over magnesium sulfate, filtered and concentrated under reduced pressure. The residue is washed with a mixture of cyclohexane/dichloromethane/ethyl acetate 1/2/2 and subsequently with a mixture of dichloromethane/diisopropylether 1/1. Then it is dried under reduced pressure to provide 4.26 g of the product as an off-white solid.

S-2,6-diamino-hexanoic acid [4-(2-{2-[4-(2-cyano-ethylamino)-furazan-3-yl]-benzoimidazol-1-yl}-acetyl)-phenyl]-amide and its hydrochloride salt (Example 1)

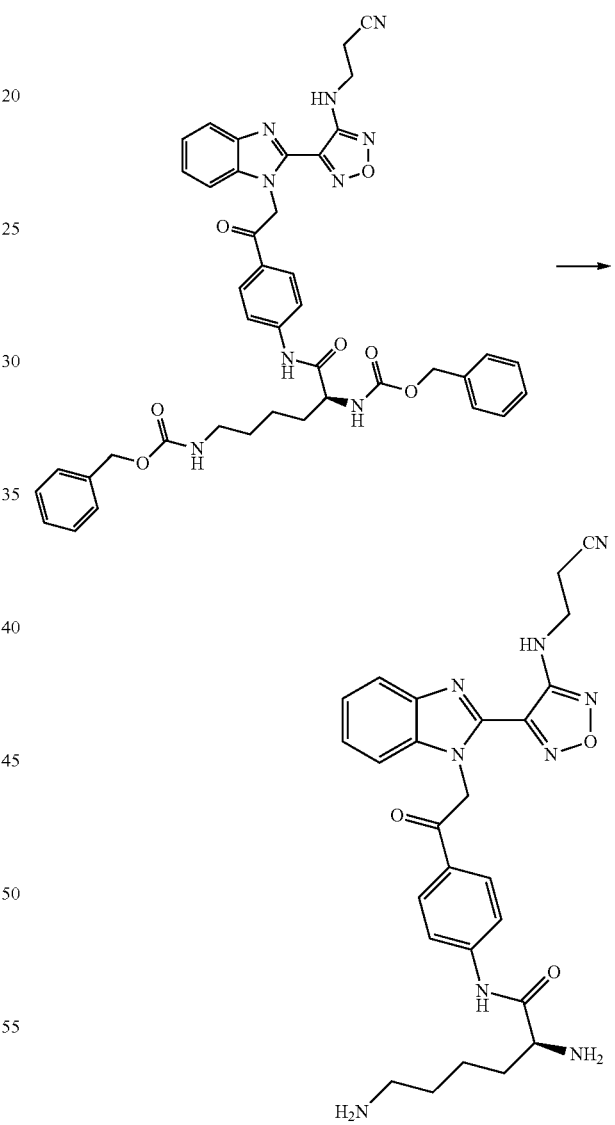

A solution of 4.77 g of S-{5-benzyloxycarbonylamino-5-[4-(2-{2-[4-(2-cyano-ethylamino) furazan-3-yl]-benzoimidazol-1-yl}-acetyl)-phenylcarbamoyl]-pentyl}-carbamic acid benzylester (6.09 mmol; 1 eq) in a mixture of 200 ml THF, 50 ml methanol and 3.5 ml 2 N hydrochloric acid is treated with 0.129 g of Pd/C (10%) and the resulting mixture is stirred for 5 h at room temperature under hydrogen atmosphere (1 atm). Then the catalyst is removed by filtration and the solvents are removed under reduced pressure. The residue is purified by MCI gel chromatography with water/acetonitrile 3/1 as eluent to provide the desired product.

Conversion into hydrochloride salt: The product is dissolved in a mixture of 50 ml dioxane and 20 ml methanol and treated with 4 ml of a 4 M solution of HCl in dioxane. Then the solvents are removed under reduced pressure. The residue is washed with a mixture of dichloromethane and diisopropylether and dried under reduced pressure to provide 1.59 g of the product as an off-white powder.

MS (ES+): 516.4 [M+H].

$^1$H-NMR (DMSO-$d_6$) ppm: 11.6 (s, 1H), 8.51 (s, 3H), 8.16 (d, J=8.3 Hz, 2H), 7.97-7.85 (m, 7H), 7.45-7.39 (m, 3H), 6.36 (s, 2H), 4.19-4.17 (m, 1H), 3.69 (q, J=6.3 Hz, 2H), 2.95 (t, J=6.3 Hz, 2H), 2.81-2.79 (m, 2H), 1.99-1.88 (m, 2H), 1.65-1.61 (m, 2H), 1.50-1.46 (m, 2H).

Procedure II

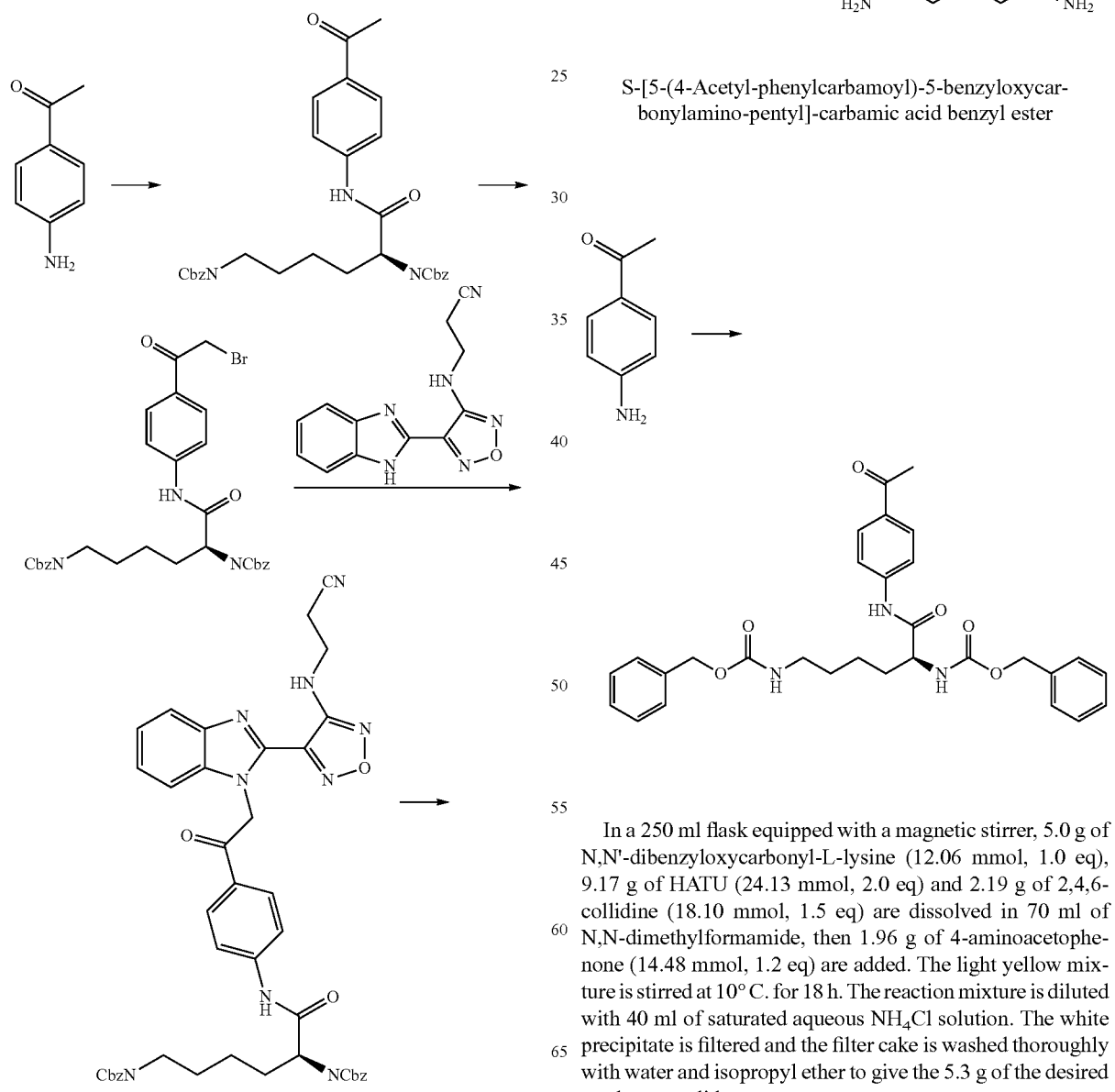

S-[5-(4-Acetyl-phenylcarbamoyl)-5-benzyloxycarbonylamino-pentyl]-carbamic acid benzyl ester In a 250 ml flask equipped with a magnetic stirrer, 5.0 g of N,N'-dibenzyloxycarbonyl-L-lysine (12.06 mmol, 1.0 eq), 9.17 g of HATU (24.13 mmol, 2.0 eq) and 2.19 g of 2,4,6-collidine (18.10 mmol, 1.5 eq) are dissolved in 70 ml of N,N-dimethylformamide, then 1.96 g of 4-aminoacetophenone (14.48 mmol, 1.2 eq) are added. The light yellow mixture is stirred at 10° C. for 18 h. The reaction mixture is diluted with 40 ml of saturated aqueous NH$_4$Cl solution. The white precipitate is filtered and the filter cake is washed thoroughly with water and isopropyl ether to give the 5.3 g of the desired product as solid.

MS (ESI+): 532.3 [M+H].

¹H-NMR (400 MHz, DMSO-d₆) ppm: 10.34 (s, 1H), 7.90 (d, J=8.8 Hz, 2H), 7.71 (d, J=8.8 Hz, 2H), 7.58 (m, 1H), 7.33-7.30 (m, 10H), 7.20 (m, 1H), 5.00 (s, 2H), 4.95 (s, 2H), 4.10 (m, 1H), 2.96 (m, 2H), 2.50 (s, 3H), 1.71-1.27 (m, 6H).

S-{5-Benzyloxycarbonylamino-5-[4-(2-bromo-acetyl)-phenylcarbamoyl]-pentyl}-carbamic acid benzyl ester S-{5-Benzyloxycarbonylamino-5-[4-(2-{2-[4-(2-cyano-ethylamino)-furazan-3-yl]-benzoimidazol-1-yl}-acetyl)-phenylcarbamoyl]-pentyl}-carbamic acid benzylester

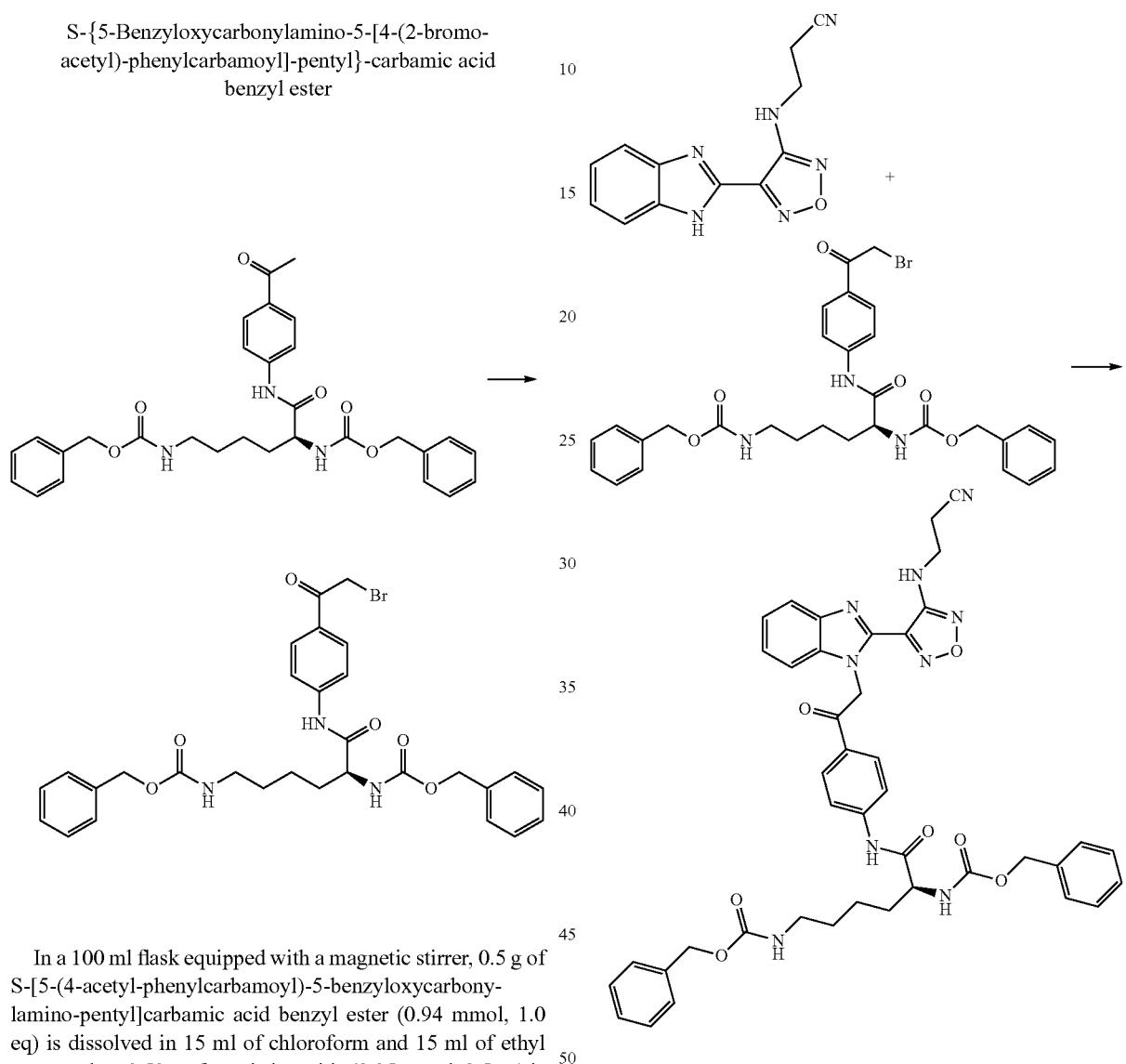

In a 100 ml flask equipped with a magnetic stirrer, 0.5 g of S-[5-(4-acetyl-phenylcarbamoyl)-5-benzyloxycarbonylamino-pentyl]carbamic acid benzyl ester (0.94 mmol, 1.0 eq) is dissolved in 15 ml of chloroform and 15 ml of ethyl acetate, then 0.53 g of cupric bromide (2.35 mmol, 2.5 eq) is added to the flask. The dark green mixture is stirred at 78° C. for 6 h. The mixture is cooled to room temperature, diluted with 40 ml of dichloromethane and filtered. The filtrate is washed with 20 ml of water and the phases are separated. The aqueous phase is extracted twice with 10 ml of dichloromethane. The combined organic phases are washed with brine, dried over sodium sulfate and concentrated to afford the crude product, which is purified by recrystallization from 3 ml of toluene to provide 350 mg of the desired product as light yellow solid.

¹H-NMR (400 MHz, DMSO-d₆) ppm: 10.39 (s, 1H), 7.95 (d, J=8.0 Hz, 2H), 7.73 (d, J=8.0 Hz, 2H), 7.60 (m, 1H), 7.39-7.20 (m, 10H), 7.13 (m, 1H), 5.00 (s, 2H), 4.95 (s, 2H), 4.81 (s, 2H), 4.15 (m, 1H), 2.97 (m, 2H), 1.62-1.28 (m, 6H).

In a 50 ml flask equipped with a magnetic stirrer, 1.3 g of S-{5-benzyloxycarbonylamino-5-[4-(2-bromo-acetyl)-phenylcarbamoyl]-pentyl}-carbamic acid benzyl ester (2.13 mmol, 1.0 eq) and 569 mg of 3-[4-(1H-benzoimidazol-2-yl)-furazan-3-ylamino]-propionitrile (2.24 mmol, 1.05 eq) are dissolved in 20 ml of N,N-dimethylformamide, then 441 mg of potassium carbonate (3.19 mmol, 1.5 eq) are added to the flask at room temperature. The mixture is stirred at room temperature for 30 min.

Then it is diluted with 20 ml of saturated aqueous NH₄Cl solution. The resulting precipitate is filtered and washed thoroughly with water and methanol to give 1.3 g of the desired product as light yellow solid.

The following compounds are prepared in analogy to above described methods either as free base or hydrochloride salt:

| Structure | | NMR | MS (ESI+) |
|---|---|---|---|
| 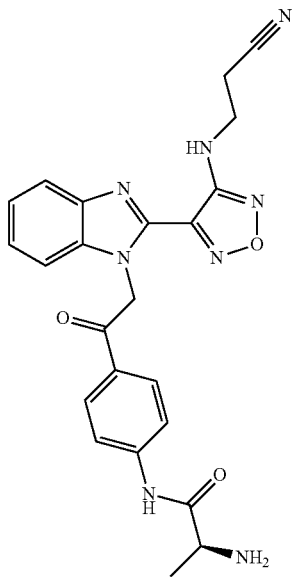 [SMILES: C[C@H](N)C(=O)Nc1ccc(C(=O)Cn2c(-c3nonc3NCCC#N)nc3ccccc32)cc1] | Example 2 Alanine Invention | $^{1}$H-NMR (DMSO-$d_6$) ppm: 8.11 (d, 2H, J = 9 Hz), 7.92-7.84 (m, 4H), 7.48-7.38 (m, 3H), 6.35 (s, 2H), 3.69 (q, 2H, J = 6.5 Hz), 3.49 (q, 1H, J = 7 Hz), 2.95 (t, 2H, J = 6.5 Hz), 1.25 (d, 3H, J = 7 Hz). | 459.2 [M + H] |
| 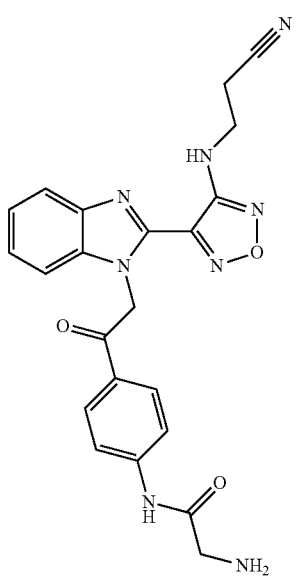 [SMILES: N#CCCNc1nonc1-c1nc2ccccc2n1CC(=O)c1ccc(NC(=O)CN)cc1] | Example 3 Glycine HCl salt Invention | $^{1}$H-NMR (DMSO-$d_6$) ppm: 11.14 (s, 1H), 8.25 (s, 3H), 8.16 (d, 2H, J = 8.5 Hz) 7.92-7.84 (m, 4H), 7.48-7.40 (m, 3H), 6.37 (s, 2H), 3.92-3.87 (m, 2H), 3.68 (q, 2H J = 6.5 Hz), 2.95 (t, 2H, J = 6.5 Hz). | 445.3 [M + H] |

| Structure | NMR | MS (ESI+) |
|---|---|---|
| 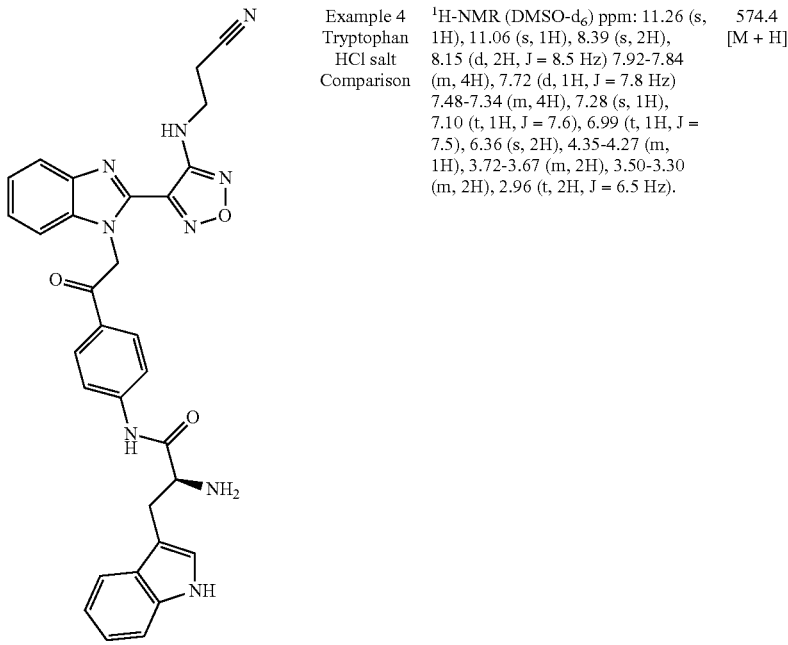 Example 4 Tryptophan HCl salt Comparison | ¹H-NMR (DMSO-$d_6$) ppm: 11.26 (s, 1H), 11.06 (s, 1H), 8.39 (s, 2H), 8.15 (d, 2H, J = 8.5 Hz) 7.92-7.84 (m, 4H), 7.72 (d, 1H, J = 7.8 Hz) 7.48-7.34 (m, 4H), 7.28 (s, 1H), 7.10 (t, 1H, J = 7.6), 6.99 (t, 1H, J = 7.5), 6.36 (s, 2H), 4.35-4.27 (m, 1H), 3.72-3.67 (m, 2H), 3.50-3.30 (m, 2H), 2.96 (t, 2H, J = 6.5 Hz). | 574.4 [M + H] |
| 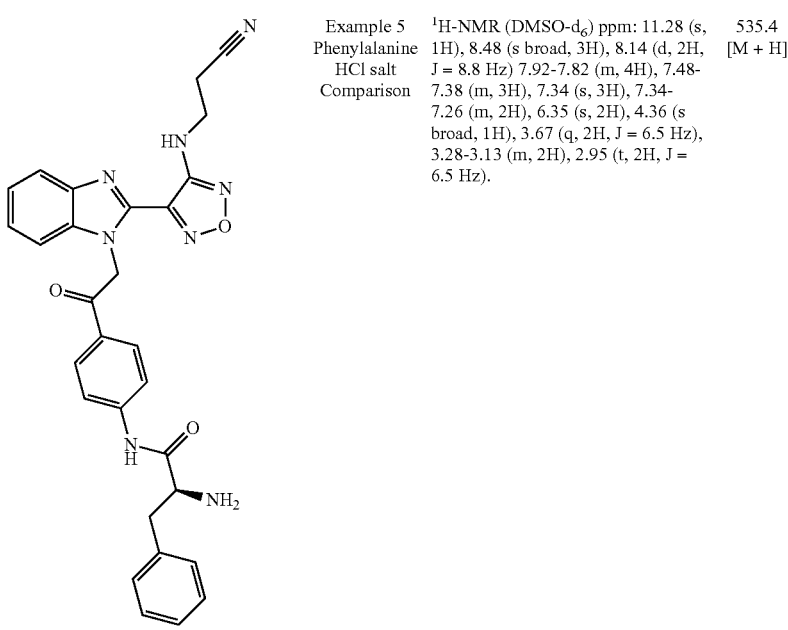 Example 5 Phenylalanine HCl salt Comparison | ¹H-NMR (DMSO-$d_6$) ppm: 11.28 (s, 1H), 8.48 (s broad, 3H), 8.14 (d, 2H, J = 8.8 Hz) 7.92-7.82 (m, 4H), 7.48-7.38 (m, 3H), 7.34 (s, 3H), 7.34-7.26 (m, 2H), 6.35 (s, 2H), 4.36 (s broad, 1H), 3.67 (q, 2H, J = 6.5 Hz), 3.28-3.13 (m, 2H), 2.95 (t, 2H, J = 6.5 Hz). | 535.4 [M + H] |

-continued
| Structure | NMR | MS (ESI+) |
|---|---|---|
| 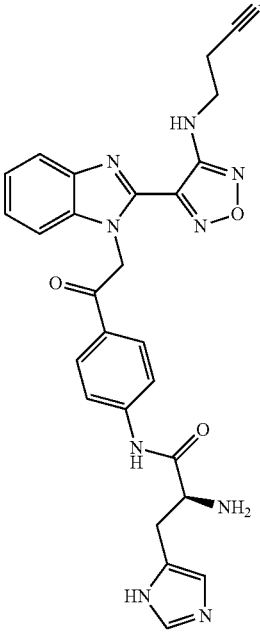 Example 6 Histidine HCl salt Comparison | ¹H-NMR (DMSO-d₆) ppm: 11.66 (s, 1H), 9.07 (s, 1H), 8.70 (s broad, 3H), 8.16 (d, 2H, J = 8.5 Hz) 7.96-7.85 (m, 4H), 7.59 (s, 1H), 7.48-7.40 (m, 3H), 6.36 (s, 2H), 4.60-4.57 (m 1H), 3.69 (q, 2H, J = 6.5 Hz), 3.48-3.32 (m, 2H), 2.95 (t, 2H, J = 6.5 Hz). | 525.4 [M + H] |
| 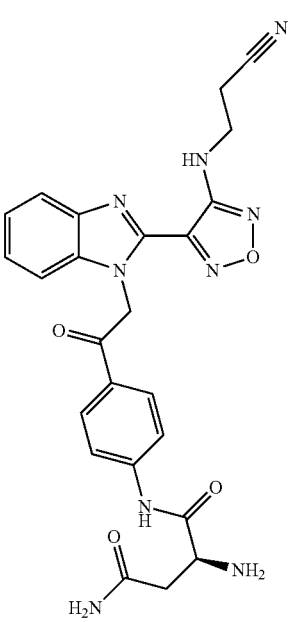 [SMILES: N#CCCNc1nonc1-c1nc2ccccc2n1CC(=O)c1ccc(NC(=O)[C@@H](N)CC(N)=O)cc1] Example 7 Asparagine HCl salt Comparison | ¹H-NMR (DMSO-d₆) ppm: 11.07 (s, 1H), 8.34 (s broad, 3H), 8.16 (d, 2H, J = 8.5 Hz) 7.92-7.85 (m, 4H), 7.75 (s, 1H), 7.48-7.40 (m, 3H), 7.31 (s, 1H), 6.36 (s, 2H), 4.35-4.29 (m, 1H), 3.69 (q, 2H, J = 6.5 Hz), 2.95 (t, 2H, J = 6.5 Hz), 2.92-2.73 (m, 2H). | 502.4 [M + H] |

-continued
| Structure | | NMR | MS (ESI+) |
|---|---|---|---|
| 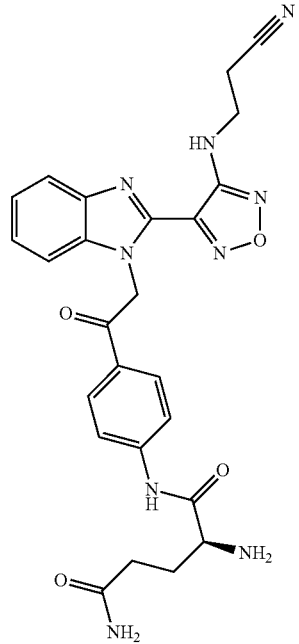 [SMILES: N#CCCNc1nonc1-c1nc2ccccc2n1CC(=O)c1ccc(NC(=O)[C@@H](N)CCC(N)=O)cc1] | Example 8 Glutamine HCl salt Comparison | ¹H-NMR (DMSO-$d_6$) ppm: 11.28 (s, 1H), 8.45 (s broad, 3H), 8.18 (d, 2H, J = 8.8 Hz) 7.92-7.85 (m, 4H), 7.51-7.40 (m, 4H), 6.37 (s, 2H), 4.16-4.09 (m, 1H), 3.69 (q, 2H, J = 6.5 Hz), 2.95 (t, 2H, J = 6.5 Hz), 2.34-2.28 (m, 2H), 2.13-2.07 (m, 2H). | 516.4 [M + H] |
| 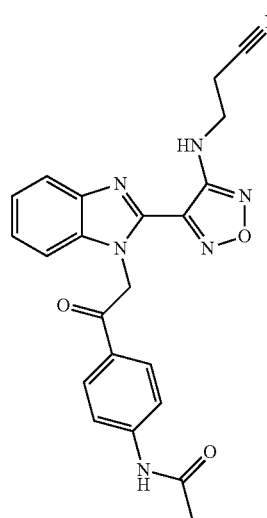 | Example 9 Arginine HCl salt Comparison | ¹H-NMR (DMSO-$d_6$) ppm: 11.56 (s, 1H), 8.49 (s broad, 3H), 8.16 (d, 2H, J = 8.5 Hz), 7.97-7.81 (m, 5H), 7.47-7.38 (m, 4H), 6.36 (s, 2H), 4.25-4.19 (m, 1H), 3.68 (q, 2H, J = 6.5 Hz), 3.25-3.15 (m, 2H), 2.95 (t, 2H, J = 6.5 Hz), 1.94-1.85 (m, 2H), 1.64-1.55 (m, 2H). | 544.3 [M + H] |

-continued
| Structure | NMR | MS (ESI+) |
|---|---|---|
| 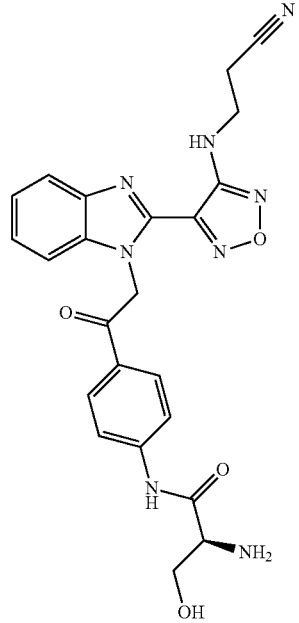 [SMILES: N#CCCNc1nonc1-c1nc2ccccc2n1CC(=O)c1ccc(NC(=O)[C@@H](N)CO)cc1] Example 10 Serine HCl salt Comparison | ¹H-NMR (DMSO-d₆) ppm : 11.18 (s, 1H), 8.35 (s broad, 2-3H), 8.14 (d, 2H, J = 8.5 Hz) 7.91-7.84 (m, 4H), 7.47-7.39 (m, 3H), 6.36 (s, 2H), 4.15-4.11 (m, 1H), 3.97-3.87 (m, 2H), 3.68 (q, 2H, J = 6.5 Hz), 2.95 (t, 2H, J = 6.3 Hz). | 475.4 [M + H] |
| 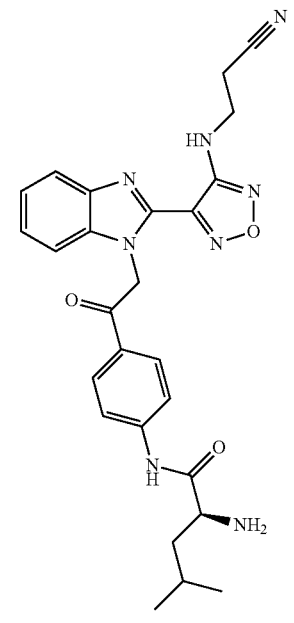 [SMILES: CC(C)C[C@H](N)C(=O)Nc1ccc(C(=O)Cn2c(-c3nonc3NCCC#N)nc3ccccc32)cc1] Example 11 Leucine Comparison | ¹H-NMR (DMSO-d₆) ppm: 8.11 (d, 2H, J = 8.9 Hz), 7.92-7.84 (m, 4H), 7.46-7.39 (m, 3H), 6.35 (s, 2H), 3.69 (q, 2H, J = 6.4 Hz), 3.40 (m, 1H) 2.95 (t, 2H, J = 6.5 Hz), 1.79 (m, 1H), 1.51 (m, 1H), 1.37 (m, 1H), 0.92 (m, 6H). | 501.2 [M + H] |

Example 12

[(4-{2-[2-(4-Amino-furazan-3-yl)-benzoimidazol-1-yl]-acetyl}-phenylcarbamoyl)-methyl]-carbamic acid tert-butyl ester

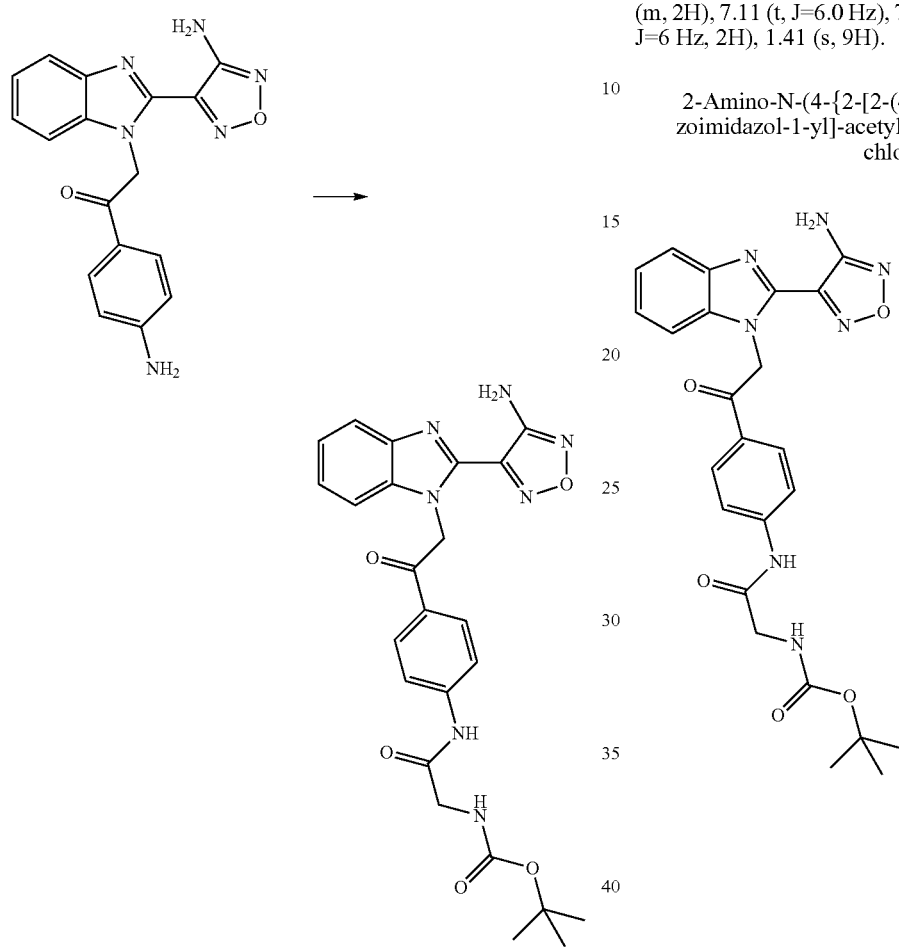

To a stirred solution of 0.06 g of N-BOC-glycine (CAS 4530-20-5) (0.34 mmol; 1.2 eq.) in 1 mL of N,N'-dimethylformamide are added 0.16 g of 2-(7-aza-1H-benzotriazole-1-yl)-1,1,3,3-tetramethyluronium hexafluorophosphate (0.43 mmol; 1.5 eq.) and 0.1 mL of triethylamine (0.71 mmol; 2.5 eq.) at room temperature. After stirring for 0.5 h at room temperature, a solution of 0.1 g of 2-[2-(4-amino-furazan-3-yl)-benzoimidazol-1-yl]-1-(4-amino-phenyl)-ethanone (CAS 798577-83-0) (0.28 mmol; 1 eq.) in 1 mL of N,N'-dimethylformamide is added. The reaction solution is stirred overnight at room temperature. Then, a solution of 0.03 g of N-BOC-glycine (0.17 mmol; 0.6 eq.) containing 0.08 g of 2-(7-aza-1H-benzotriazole-1-yl)-1,1,3,3-tetramethyluronium hexafluorophosphate (HATU) (0.22 mmol; 0.75 eq.) and 0.05 mL of triethylamine (0.35 mmol; 1.25 eq.) in 0.5 mL of N,N'-dimethylformamide is added to the reaction solution at room temperature. The same mixture is added again after additional 24 h and additional 8 h. The reaction mixture is then further stirred for 64 h (total reaction time 120 h). The reaction mixture is diluted with ethyl acetate (10 mL) and then washed with water (10 mL), 10% citric acid aqueous solution (10 mL), brine (2×5 mL), dried over magnesium sulfate, filtered and concentrated to dryness to give crude product. The crude product is subjected to silica gel column chromatography (eluent: ethyl acetate/cyclohexane=1/1 to 4/1). The obtained material is recrystallized from dichloromethane to afford 0.085 g of the desired product as a white powder.

MS (ESI+): 492.4 [M+H].

$^1$H-NMR (DMSO-$d_6$) ppm: 10.40 (s, 1H), 8.12 (d, J=8.8 Hz, 2H), 7.88 (d, J=7.6 Hz, 2H), 7.82 (d, J=8.8 Hz; 2H), 7.40 (m, 2H), 7.11 (t, J=6.0 Hz), 7.00 (s, 2H), 6.33 (s, 2H), 3.79 (d, J=6 Hz, 2H), 1.41 (s, 9H).

2-Amino-N-(4-{2-[2-(4-amino-furazan-3-yl)-benzoimidazol-1-yl]-acetyl}-phenyl)-acetamide hydrochloride salt

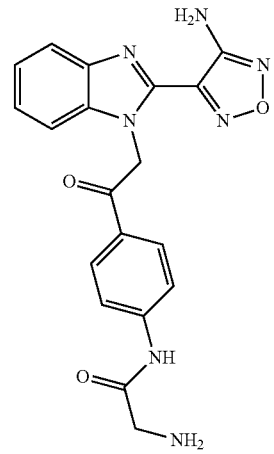

To a stirred solution of 0.045 g of [(4-{2-[2-(4-amino-furazan-3-yl)-benzoimidazol-1-yl]-acetyl}-phenylcarbamoyl)-methyl]-carbamic acid tert-butyl ester (0.09 mmol; 1 eq.) in 0.5 mL of 1,4-dioxane are added dropwise 0.11 mL of a 4M HCl solution in 1,4-dioxane (0.44 mmol; 5 eq.) at room temperature. The reaction mixture is stirred for 2 h at room temperature. Then, 5 mL of diisopropylether are added and the resulting suspension is filtered, washed with diisopropylether (2×2 mL) and dried under reduced pressure to give 0.04 g of crude material. The crude solid is subjected to MCI gel column chromatography eluting with a mixture water/acetonitrile (85/15 to 70/30) containing 0.05% of HCl, to afford 0.014 g of the desired product as an orange powder.

MS (ESI+): 392.4 [M+H].

$^1$H-NMR (DMSO-d$_6$) ppm: 11.21 (s, 1H), 8.29 (br. s., 3H), 8.16 (d, J=8.8 Hz, 2H), 7.88 (d, J=8.8 Hz, 2H), 7.84 (m, 2H), 7.41 (m, 2H), 7.1-6.9 (m, 2H), 6.36 (s, 2H), 3.95 (m, 2H).

Example 13 (Comparison)

4-[1-(2-Trimethylsilanyl-ethoxymethyl)-1H-benzoimidazol-2-yl]-furazan-3-ylamine

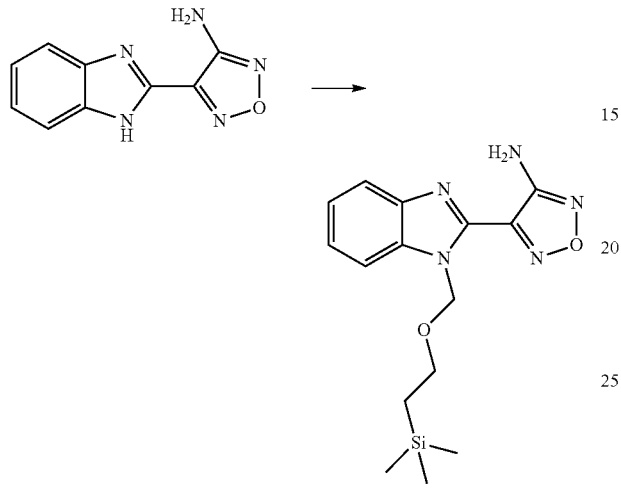

To a stirred suspension of 0.5 g of 4-(1H-benzoimidazol-2-yl)-furazan-3-ylamine (CAS 332026-86-5) (2.49 mmol; 1.0 eq.) in 15 mL of dry tetrahydrofuran cooled to 0° C. are added portionwise 0.075 g of sodium hydride (2.98 mmol; 1.2 eq.). After stirring for 10 min at 0-5° C., the resulting clear solution is treated with 0.54 mL of 2-(trimethylsilyl) ethoxymethyl chloride (2.91 mmol; 1.17 eq.). The reaction solution is stirred for 0.5 h at 0-5° C. and then diluted with 30 mL of ethyl acetate. The solution is washed with water (20 mL) and brine (20 mL), dried over magnesium sulfate, filtered and concentrated to dryness. The oily residue is triturated in diisopropylether (10 mL) and the solvent is removed under reduced pressure to give 0.78 g of the desired product as an off-white solid.

MS (ESI+): 332.4 [M+H].

$^1$H-NMR (DMSO-d$_6$) ppm: 8.01 (m, 2H), 7.65-7.53 (m, 2H), 7.13 (s, 2H), 6.22 (s, 2H), 3.72 (t, J=8.0 Hz, 2H), 0.96 (t, J=8.0 Hz, 2H), 0.01 (s, 9H).

({4-[1-(2-Trimethylsilanyl-ethoxymethyl)-1H-benzoimidazol-2-yl]-furazan-3-ylcarbamoyl}-methyl)-carbamic acid benzyl ester

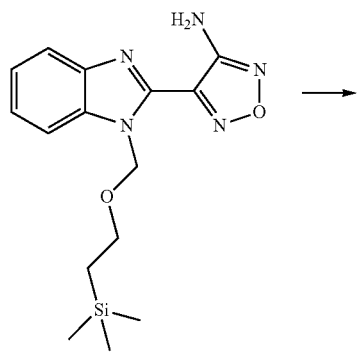

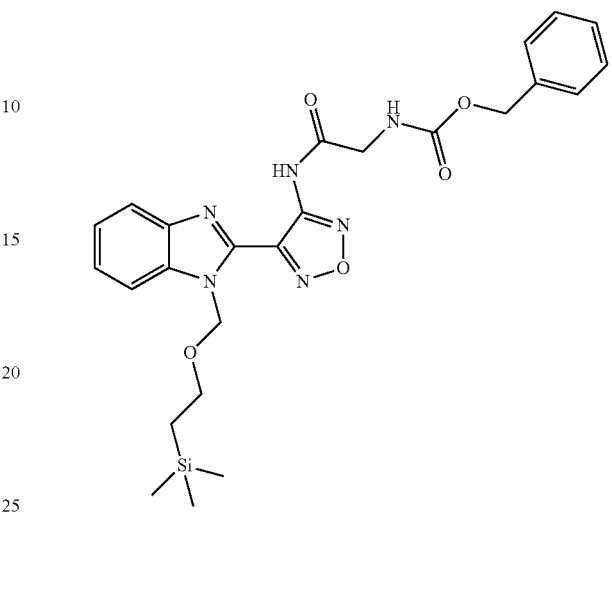

To a stirred suspension of 1.42 g of N-Z-glycine (CAS 1138-80-3) (6.65 mmol; 2.9 eq.) in 4 mL of dichloromethane are added dropwise 1.23 mL of 1-chloro-N,N-2-trimethyl-1-propenylamine (9.17 mmol; 4 eq.) at room temperature. The resulting clear solution is stirred for 1 h and then concentrated to dryness to give the corresponding acid chloride as colorless oil. In a sealed-tube, a stirred solution of 0.8 g of 4-[1-(2-trimethylsilanyl-ethoxymethyl)-1H-benzoimidazol-2-yl]-furazan-3-ylamine (2.29 mmol; 1.0 eq.) in 10 mL of tetrahydrofuran cooled to 0-5° C. is treated portionwise with 0.29 g of sodium hydride (11.5 mmol; 5 eq.) and then with a solution of the freshly prepared acid chloride in 5 mL of tetrahydrofuran. At the end of the addition, the ice bath is removed and the cap is locked. The solution is heated to 70° C. and stirred for 21 h at this temperature. The reaction mixture is allowed to cool down to room temperature and is then diluted with 40 mL of ethyl acetate. Water (30 mL) is carefully added and the two layers are separated. The organic phase is washed with brine (2×20 mL), dried over magnesium sulfate, filtered and concentrated to dryness under reduced pressure to give the crude product. The crude product is purified by silica gel column chromatography (eluent: ethyl acetate/cyclohexane=5/95 to 55/45) to give 0.57 g of the desired product as a white solid.

MS (ESI+): 523.4 [M+H].

$^1$H-NMR (DMSO-d$_6$) ppm: 11.76 (s, 1H), 8.29 (t, J=5.6 Hz, 1H), 7.89 (d, J=8.2 Hz, 2H), 7.78 (d, J=8.2 Hz, 2H), 7.53-7.29 (m, 5H), 6.08 (s, 2H), 5.08 (s, 2H), 4.02 (J=5.6 Hz, 2H), 3.59 (t, J=8.0 Hz, 2H), 0.84 (t, J=8.0 Hz, 2H), 0.01 (s, 9H).

{[4-(1H-Benzoimidazol-2-yl)-furazan-3-ylcarbamoyl]-methyl}-carbamic acid benzyl ester

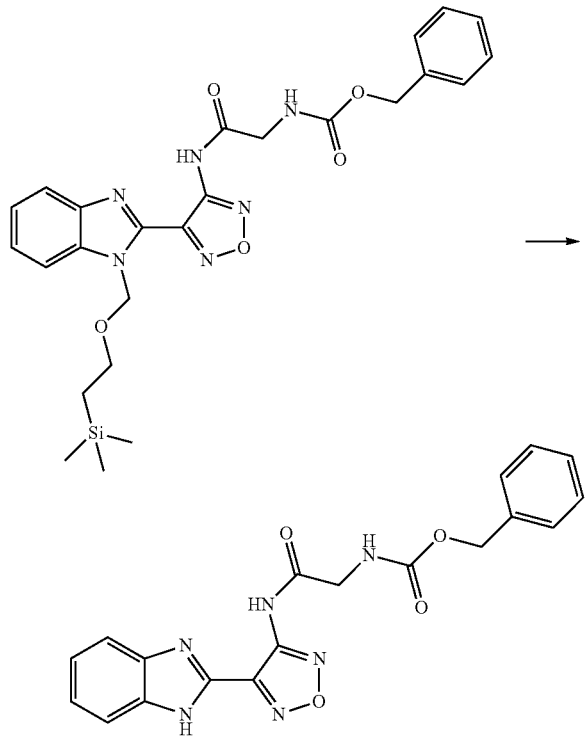

0.55 g of ({4-[1-(2-trimethylsilanyl-ethoxymethyl)-1H-benzoimidazol-2-yl]-furazan-3-ylcarbamoyl}-methyl)-carbamic acid benzyl ester (1.00 mmol; 1 eq.) are added portionwise to 2.75 mL of trifluoroacetic acid (35.3 mmol; 35 eq.) at room temperature. The solution is stirred for 1 h and then concentrated to dryness under reduced pressure. The residue is dissolved in 3 mL of THF. Then, 2 mL of an aqueous solution of 8% sodium hydrogen carbonate are added. The resulting biphasic mixture is heated to 50° C. and vigorously stirred for 1.5 h. Then, the mixture is diluted with 10 mL of ethyl acetate and 5 mL of water and the organic layer is separated, washed with brine (5 mL), dried over magnesium sulfate, filtered and concentrated to dryness under reduced pressure to give 0.4 g of the desired product as a white solid.

MS (ESI+): 393.3 [M+H].

$^1$H-NMR (DMSO-d$_6$) ppm: 11.65 (s, 1H), 8.26 (t, J=6.0 Hz, 1H), 7.67 (d, J=8.0 Hz, 2H), 7.38-7.30 (m, 7H), 5.10 (s, 2H), 4.04 (d, J=6.0 Hz, 2H).

[4-(2-{2-[4-(2-Benzyloxycarbonylamino-acetylamino)-furazan-3-yl]-benzoimidazol-1-yl}-acetyl)-phenyl]-carbamic acid benzyl ester

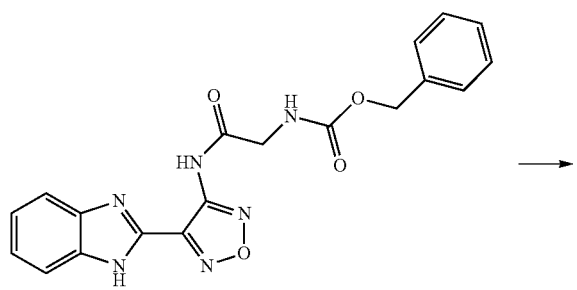

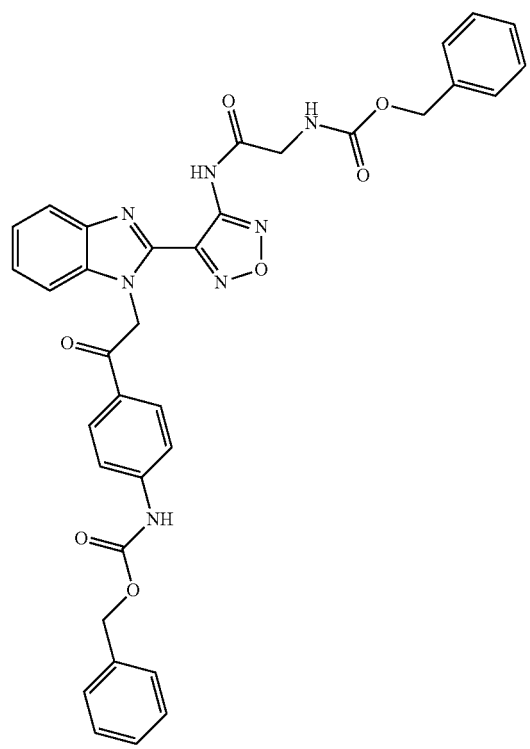

To a stirred solution of 0.4 g of {[4-(1H-benzoimidazol-2-yl)-furazan-3-ylcarbamoyl]-methyl}-carbamic acid benzyl ester (0.97 mmol, 1 eq.) in 6 mL of N,N'-dimethylformamide are added 0.2 g of potassium carbonate (1.4 mmol; 1.45 eq.) at room temperature followed by the addition of 0.41 g of [4-(2-bromo-acetyl)-phenyl]-carbamic acid benzyl ester (CAS 157014-41-0) (1.16 mmol; 1.2 eq.). The reaction mixture is stirred for 2 h at room temperature and is then diluted with 20 mL of ethyl acetate. The solution is washed with water (2×10 mL) and brine (2×10 mL), dried over magnesium sulfate, filtered and concentrated to dryness under reduced pressure. The residue is then dissolved in hot ethyl acetate (2 mL) and the solution is placed in an ice-bath. After 0.5 h, the resulting suspension is filtered and the solid is washed with cold ethyl acetate (1 mL) to afford 0.2 g of the desired product as a white powder.

MS (ESI+): 660.5 [M+H].

$^1$H-NMR (DMSO-d$_6$) ppm: 11.80 (s, 1H), 10.35 (s, 1H), 8.34 (t, J=4.6 Hz, 1H), 8.11 (d, J=8.0 Hz, 2H), 7.80 (m, 2H), 7.73 (d, J=8.0 Hz, 2H), 7.50-7.32 (m, 12H), 6.38 (s, 2H), 5.23 (s, 2H), 5.12 (s, 2H), 4.06 (d, J=4.6 Hz, 2H).

2-Amino-N-(4-{1-[2-(4-amino-phenyl)-2-oxo-ethyl]-1H-benzoimidazol-2-yl}-furazan-3-yl)-acetamide hydrochloride salt

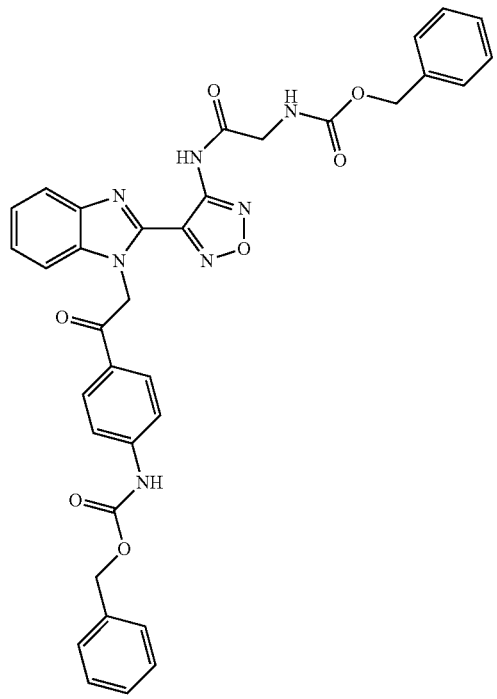

A mixture of 0.2 g of [4-(2-{2-[4-(2-benzyloxycarbonylamino-acetylamino)-furazan-3-yl]-benzoimidazol-1-yl}-acetyl)-phenyl]-carbamic acid benzyl ester (0.29 mmol; 1 eq.) in 2 mL of tetrahydrofuran and 2 mL of methanol containing 0.19 mL of a solution of 4M HCl in 1,4-dioxane (0.86 mmol; 3 eq.) and 0.046 g of 10% Pd/C (0.04 mmol; 0.14 eq.) is stirred for 7 hours under hydrogen atmosphere at room temperature. Then the mixture is filtered and the filtrate is concentrated under reduced pressure. The residue is suspended in 2 mL of a mixture of dichloromethane/diisopropylether (1/1, v/v) and the suspension is filtered. The solid is washed with 2 mL of diisopropylether and dried under reduced pressure to give the crude product. The solid is purified by MCI gel column chromatography (eluent water/acetonitrile=75/25 to 65/35, containing 0.1% of HCl) to afford 0.02 g of the desired product as a light brown powder.

MS (ESI+): 392.3 [M+H].
$^1$H-NMR (DMSO-$d_6$) ppm: 11.29 (s, 1H), 8.46 (br. s., 3H), 7.95-7.83 (m, 4H), 7.41 (m, 2H), 6.98 (d, J=8.4 Hz, 2H), 6.22 (s, 2H), 4.23 (m, 2H).

Example 14 (Comparison)

N'-[4-(2-{2-[4-(2-Cyano-ethylamino)-furazan-3-yl]-benzoimidazol-1-yl}-acetyl)-phenyl]-N,N-dimethyl-formamidine

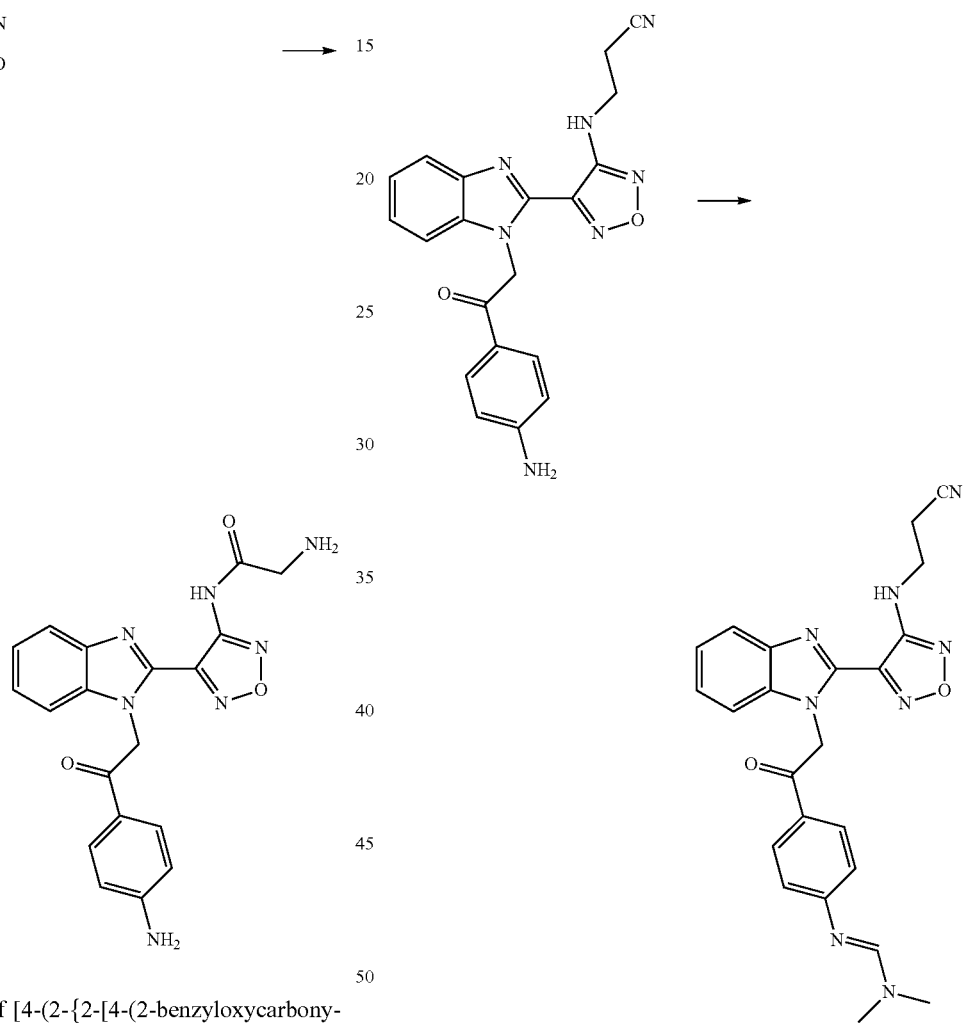

A solution of 0.05 ml N,N-diisopropylethylamine in 1 mL of N,N-dimethylformamide is slowly added to a solution of 116 mg (0.3 mmol) 3-(4-{1-[2-(4-amino-phenyl)-2-oxo-ethyl]-1H-benzoimidazol-2-yl}-furazan-3-ylamino)-propionitrile and 459 mg (0.3 mmol) phosphorus oxychloride in 3 mL of N,N-dimethylformamide at −10° C. After the addition, the mixture is allowed to warm to room temperature and stirred for three days. Then, saturated aqueous ammoniumchloride solution is added and the reaction mixture is extracted with dichloromethane. A precipitate is formed in the dichloromethane phase. This precipitate is collected by filtration, washed with water and dichloromethane, and dried under reduced pressure. The residue is solved in acetonitrile and the solution is added to a 2 N solution of sodium hydroxide in water at 0° C. The resulting pH value is above 11. The mixture is stirred at room temperature for 1 h. The formed precipitate is collected by filtration, washed with water and acetonitrile, and dried under reduced pressure to provide 89 mg of the desired product.

MS (ESI+): 443.2 [M+H].

$^1$H-NMR (DMSO-$d_6$) ppm: 8.00-7.97 (m, 3H), 7.91-7.83 (m, 2H), 7.49-7.38 (m, 3H), 7.11 (d, J=8.5 Hz, 2H), 6.32 (s, 2H), 3.69 (q, J=6.5 Hz, 2H), 3.09 (s, 3H), 2.99 (s, 3H), 2.95 (t, J=6.5 Hz, 2H).

Example 15 (Comparison)

[4-(2-{2-[4-(2-Cyano-ethylamino)-furazan-3-yl]-benzoimidazol-1-yl}-acetyl)-phenyl]-sulfamic acid sodium salt

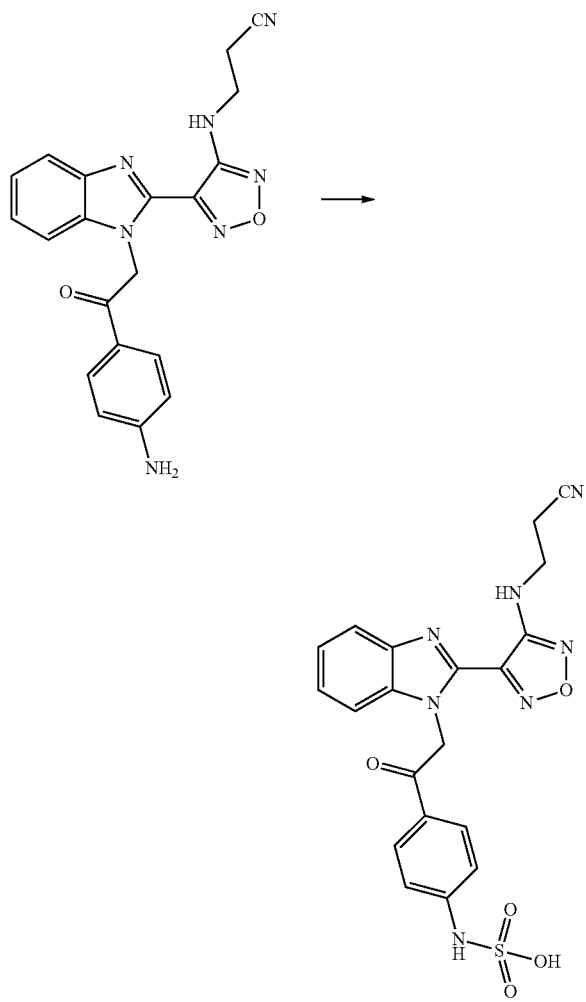

50 µL (0.75 mmol) of chlorosulfonic acid are added dropwise to 603 µL (7.5 mmol) pyridine under cooling in an ice/ethanol bath. After stirring the mixture for 1 h, 116 mg (0.3 mmol) 3-(4-{1-[2-(4-amino-phenyl)-2-oxo-ethyl]-1H-benzoimidazol-2-yl}-furazan-3-ylamino)-propionitrile dissolved in a small amount of pyridine are added and the mixture is stirred at room temperature overnight. Aqueous 1 N sodium hydroxide solution is added until pH10 is reached. Then, the mixture is concentrated under reduced pressure. The residue is treated with water and the solid product (143 mg) is obtained by centrifugation, followed by washing with water and drying under reduced pressure.

MS (ESI+): 468.1 [M+H].

$^1$H-NMR (DMSO-$d_6$) ppm: 8.89 (s, 1H), 7.90-7.81 (m, 4H), 7.49-7.37 (m, 3H), 7.15 (d, J=8.5 Hz, 2H), 6.25 (s, 2H), 3.69 (q, J=6.5 Hz, 2H), 2.95 (t, J=6.5 Hz, 2H).

Methods for Testing of Compounds of the Invention
Determination of Kinetic Solubility:

Compounds, provided as 20 mM or 10 mM stock solutions in 100% DMSO, are diluted 1:40 in aqueous buffer to a concentration of 0.5 mM or 0.25 mM, respectively, with 2.5% residual DMSO. The pH 6.5 buffer consists of 0.05 M 3-(N-morpholino)-2-hydroxypropanesulfonic acid (MOPSO) adjusted to the target pH with NaOH. Buffers at pH 5 and pH 3 are prepared from commercially available concentrates (Titrisol®, Merck). The samples are then incubated at room temperature for 6 hours with gentle shaking followed by vacuum filtration through a MultiScreen DV plate (Durapore hydrophilic PVDF membrane, 0.65 µm pore size, Millipore). The filtrates are adjusted to 20% acetonitrile and analyzed by UV spectroscopy to obtain the absorption maximum and the corresponding wavelength. The concentration of compound in the filtrate is calculated based on the linear part of a standard curve constructed using 3 to 5 known concentrations of each sample in aqueous buffer supplemented with 20% acetonitrile.

All amino acid derived prodrugs show an improved aqueous solubility compared to the parent drug. The highest solubility is obtained at pH 3 for all prodrugs. At pH 5 and pH 6.5, the lysine prodrug shows the highest solubility.

| Example | pH | C eff (µM) |
|---|---|---|
| 3-(4-{1-[2-(4-Amino-phenyl)-2-oxo-ethyl]-1H-benzoimidazol-2-yl}-furazan-3-ylamino)-propionitrile Parent Drug | 6.5 | <10 |
|  | 5.0 | <10 |
|  | 3.0 | <10 |
| Leu | 6.5 | 20 |
| Example 11 | 5.0 | 37 |
| Comparison | 3.0 | 189 |
| Ala | 6.5 | 91 |
| Example 2 | 5.0 | 55 |
|  | 3.0 | >200 |
| Gly | 6.5 | 106 |
| Example 3 | 5.0 | 71 |
|  | 3.0 | >200 |
| Lys | 6.5 | 190 |
| Example 1 | 5.0 | >200 |
|  | 3.0 | >200 |

In Vivo Pharmacokinetic Studies:

The compounds are evaluated in vivo after intravenous administration to male NMRI mice using the Vena saphena screening method.

A dose of 1 mg/kg of the compound is administered i.v. as a bolus (5 mL/kg). Serial blood samples (40 µL) are drawn after puncture of the saphenous vein and collected in a sodium heparin coated capillary tube from two mice per time point at pre-dose, 5 min, 15 min, 30 min, 45 min, 1 h, 2 h, 4 h, 6 h, 8 h and 24 h after intravenous administration.

Blood samples are weighed and the blood quenched in 300 µl stop solution consisting of acetonitrile/water (80:20) and an internal standard.

Blood concentrations of the compound (prodrug) and its parent drug are determined using LC-MS/MS analysis with a limit of quantification of 4 to 40 ng/mL.

Calculation of the Area Under the Curve (AUC)

Mean arithmetic plasma/blood concentrations are calculated using BLQ (below limit of quantitation)–value of zero if necessary.

Mean $AUC_{infIV}$ [ng*h/mL] The area under the blood concentration-time curve for a mean normalized (1 mg/kg) iv application from time zero to the last sampling time with a concentration above the limit of quantification.

Mean $AUC_{infIV}$ is calculated according to the linear trapezoidal rule.

In a study mice are intravenously treated with prodrugs according to the invention, followed by determination of the blood concentration of the drug. For comparison, similar amide prodrugs based on other natural amino acids are also tested.

AUC value is a measure for the total exposure of the animals to the drug.

It is found that lysine, glycine and alanine derived prodrugs give at least 50% higher AUC values of the parent drug than the comparative prodrugs based on the chemically most closely related natural amino acids. This remarkable increase in exposure to the parent drug after administration of the prodrugs according to the invention is quite surprising and unexpected.

| Prodrug Amino Acid | AUC of parent drug 3-(4-{1-[2-(4-amino-phenyl)-2-oxo-ethyl]-1H-benzoimidazol-2-yl}-furazan-3-ylamino)-propionitrile [ng h/ml] |
|---|---|
| Lys (invention) Example 1 | 1090 |
| Ala (invention) Example 2 | 1044 |
| Gly (invention) Example 3 | 1000 |
| Trp (comparison) Example 4 | 276 |
| Phe (comparison) Example 5 | 445 |
| His (comparison) Example 6 | 598 |
| Asn (comparison) Example 7 | 455 |
| Gln (comparison) Example 8 | 552 |
| Arg (comparison) Example 9 | 660 |
| Ser (comparison) Example 10 | 425 |
| Leu (comparison) Example 11 | 680 |

After intravenous administration of Example 14 and Example 15 to mice, no significant levels of the parent drug 3-(4-{1-[2-(4-amino-phenyl)-2-oxo-ethyl]-1H-benzoimidazol-2-yl}-furazan-3-ylamino)-propionitrile are detected.

Pharmacokinetic Studies in Xenografted Mice

CD-1 Nu/Nu female mice implanted with the human colon carcinoma SW480 cell line are treated with either the "Parent Drug", i.e. 3-(4-{1-[2-(4-amino-phenyl)-2-oxo-ethyl]-1H-benzoimidazol-2-yl}-furazan-3-ylamino)-propionitrile, or "Example 1" i.e. S-2,6-diamino-hexanoic acid [4-(2-{2-[4-(2-cyano-ethylamino)-furazan-3-yl]-benzoimidazol-1-yl}-acetyl)-phenyl]-amide hydrochloride salt, when the tumor size reached approximately 150 mm$^3$+/−10%. Mice (33 per compound) are treated i.v. (5 mL/kg) once a week with 10 mg/kg "Parent Drug" (vehicle: NMP 6.7%, Solutol HS15 10%, Kolidon12 8.3% in demineralized water) or 24.5 mg/kg "Example 1" (vehicle: sodium acetate in saline qs pH 5) for 2 weeks. Due to body weight losses >10% in a few animals, the application volumes are subsequently reduced to 4 mL/kg resulting in doses of 8 mg/kg "Parent Drug" and 19.6 mg/kg "Example 1" for a further week.

After the 4$^{th}$ application (4$^{th}$ week), three mice/sampling point from the "Parent Drug" and "Example 1" groups are culled before and 5 min, 15 min, 30 min, 45 min, 1 h, 1.5 h, 2 h, 4 h, 6 h and 24 h post-administration. Blood is collected by cardiac puncture into K$_3$EDTA tubes kept on ice until centrifugation at 4° C. Plasma is stored at −20° C. At necropsy, tumors are removed and weighed. Tumors are stored at −20° C. Plasma and tumor samples are analyzed by LC-MS/MS. Pharmacokinetic parameters are calculated using WinNonLin 5.2. All results for "Example 1" represent the free base.

Results

Tumor distribution of the "Parent Drug", administered either as such or in form of "Example 1", is demonstrated. Tumor concentrations are detected already in the first sampling time at 5 min post-administration. The tumor/plasma ratio is approximately 1. There is no accumulation in tumors, as the concentration in tumor parallels the concentration in plasma. However, after administration of "Example 1", the exposure of tumors to the "Parent Drug" and "Example 1" is almost two times longer (half life $T_{1/2}$ of 8.3 and 9.6 h) compared to the exposure after administration of the drug ($T_{1/2}$ of 5.4 h).

Pharmacokinetic Parameters of "Parent Drug" in Plasma and Tumor Tissue after I.V. Administration of 8 mg/kg "Parent Drug" to Xenografted Mice

|  | Plasma | Tumors |
|---|---|---|
| $C_{max}$ (ng/mL) | 11000 | 3210 |
| $AUC_{last}$ (ng · h/mL) | 44800 | 45500 |
| $T_{1/2}$ (h) | 3.2 | 5.4 |

Pharmacokinetic Parameters of "Parent Drug" in Plasma and Tumor Tissue after I.V. Administration of 19.6 mg/kg "Example 1" to Xenografted Mice

|  | Plasma | Tumors |
|---|---|---|
| $C_{max}$ (ng/mL) | 9290 | 5680 |
| $AUC_{last}$ (ng · h/mL) | 47400 | 56300 |
| $T_{1/2}$ (h) | 6.8 | 8.3 |

Pharmacokinetic Parameters of "Example 1" in Plasma and Tumor Tissue after I.V. Administration of 19.6 mg "Example 1" to Xenografted Mice

|  | Plasma | Tumors |
|---|---|---|
| $C_{max}$ (ng/mL) | 81900 | 6010 |
| $AUC_{last}$ (ng · h/mL) | 21100 | 29300 |
| $T_{1/2}$ (h) | 5.5 | 9.6 |

In Vivo Efficacy Studies:

Mice bearing SW480 colorectal cancer xenografts are used to test and compare the anti-cancer efficacy and tolerability of intravenous (i.v.) application of the prodrug according to Example 1 (S-2,6-diamino-hexanoic acid [4-(2-{2-[4-(2-cyano-ethylamino)-furazan-3-yl]-benzoimidazol-1-yl}-acetyl)-phenyl]-amide hydrochloride salt) and the corresponding parent drug" (3-(4-{1-[2-(4-amino-phenyl)-2-oxo-ethyl]-1H-benzoimidazol-2-yl}-furazan-3-ylamino)-propionitrile) at the maximum tolerated dose level (MTD). Prior to the efficacy experiment, a determination of the MTD of each compound administered once weekly is performed in non-tumor-bearing nude mice of the same strain. Administration of 24.5 mg/kg prodrug and 10 mg/kg parent drug, given as an i.v. bolus once weekly, results in body weight losses >10% in a few animals in both groups. The MTDs in tumor-bearing mice are, therefore, determined to be 15-20% lower, resulting in doses of 21 mg/kg prodrug and 8 mg/kg parent drug. Human colorectal carcinoma cells (SW480) are injected subcutaneously (4×10⁶ cells) into the back of 4-8-week old athymic nude mice. Tumor volumes are determined from calliper measurements of tumor length (L) and width (1) according to the formula (L×l²)/2. Tumors are allowed to expand to a volume of 200 mm³ (±10%) before treatment start. The prodrug and parent drug are administered i.v. for 24 days, either once per week at 21 mg/kg and 8 mg/kg, respectively, or three times a week (d1/4/7) at 7.1 mg/kg and 2.7 mg/kg, respectively (both schedules represent the same total weekly dose). Tumor volume and body weight are monitored daily.

Using the once weekly schedule (cf. FIG. 1), the prodrug elicits a final T/C (ratio of tumor volume in the treatment group vs. the control group) at day 24 of 34% (p<0.001 vs controls) in comparison to 45% for the parent drug (p<0.001 vs controls). Using the three times per week schedule (cf. FIG. 2), the prodrug elicits a final T/C (day 24) of 26% (p<0.001 vs control) in comparison to 54% for the parent drug (p=0.002 vs control). The body weight changes observed were minor in all treatment groups. However, one animal in the parent drug-group (three times per week treatment) died at day 10.

The three times per week administration of prodrug provides a significant better efficacy in the mouse xenograft cancer model than a corresponding administration of the parent drug (p<0.05).

FIG. 1 provides a graphical representation of the changes in mean tumor volume during the time of treatment when using the administration schedule, wherein prodrug and parent drug are given once weekly for 24 days at doses of 21 mg/kg and 8 mg/kg, respectively, with appropriate vehicle controls (5 ml/kg) administered with the same schedule. Data points represent mean values+/−SEM (n=7-8 animals, each animal was engrafted with one tumor).

FIG. 2 provides a graphical representation of the changes in mean tumor volume during the time of treatment when using the administration schedule, wherein prodrug and parent drug are given three times per week (d1/4/7) for 24 days at doses of 7.1 mg/kg and 2.7 mg/kg in 5 ml/kg, respectively, with appropriate vehicle controls (5 ml/kg) administered with the same schedule. Data points again represent mean values+/−SEM (n=7-8 animals, each animal was engrafted with one tumor).

Comparison of the Prodrug-Drug Conversion of the Prodrug According to Example 12 (Present Invention) and the Prodrug According to Example 13 (Comparison) in Full Blood Procedure:

495 μL fresh heparinised rat blood are spiked with 5 μL of a 1 mg/mL DMSO solution of the analyte (prodrug) at 37° C. After t=0, 5, 15, 30, 60 and 120 min, a blood sample is taken and precipitated. Therefore to 50 μL blood sample or spiked blood sample 150 μL acetonitrile containing an internal standard are added. Samples are centrifuged and 20 μl of the supernatant are injected into the HPLC system for determination of compound concentration (prodrug and parent drug) by LC-MS/MS analysis.

For calibration, a standard curve is prepared with a compound concentration range from 10 to 10000 ng/mL in fresh heparine rat blood. Therefore the blood is spiked (2 μL DMSO solution in 198 μL fresh rat blood) and precipitated like unknown samples.

Results:
The prodrug 2-amino-N-(4-{2-[2-(4-amino-furazan-3-yl)-benzoimidazol-1-yl]-acetyl}-phenyl)-acetamide according to the present invention (Example 12) is completely converted into its parent drug 2-[2-(4-amino-furazan-3-yl)-benzoimidazol-1-yl]-1-(4-amino-phenyl)-ethanone in rat blood after 120 min, whereas the conversion of the regioisomer of said prodrug 2-amino-N-(4-{1-[2-(4-amino-phenyl)-2-oxo-ethyl]-1H-benzoimidazol-2-yl}-furazan-3-yl)-acetamide (Example 13) is remarkably lower (approximately 74% after 120 min).

The invention claimed is:

1. A compound of formula (II)

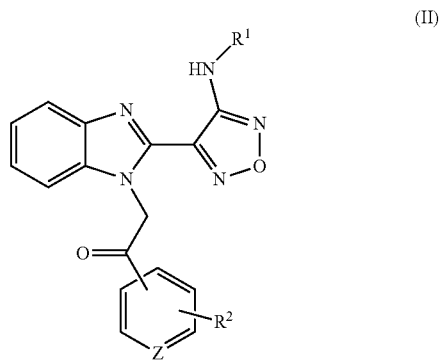

wherein

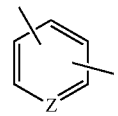

represents 1,4-phenylene or a group of formula

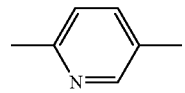

R¹ represents hydrogen, lower alkylcarbonyl, hydroxy-lower alkyl or cyano-lower alkyl; and R² is selected from the group consisting of:

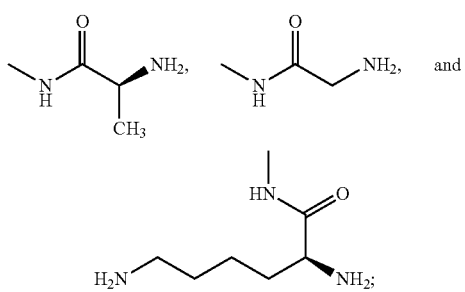

or pharmaceutically acceptable salts thereof.

2. A compound of formula (II) according to claim 1 which is not a salt.

3. A compound according to claim 1 wherein
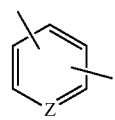
represents 1,4-phenylene.
4. A compound of claim 1 wherein
$R^1$ represents hydrogen or cyano-lower alkyl.
5. The compound of claim 4 selected from the group consisting of the compounds of formulae
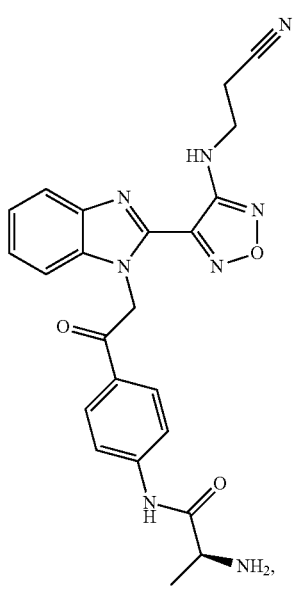
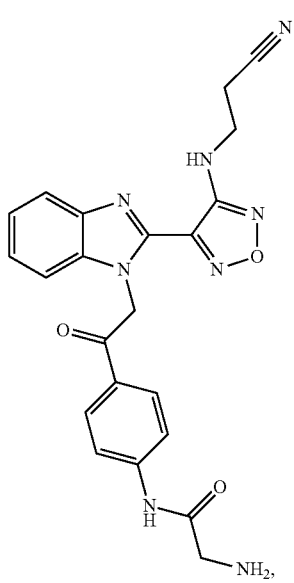
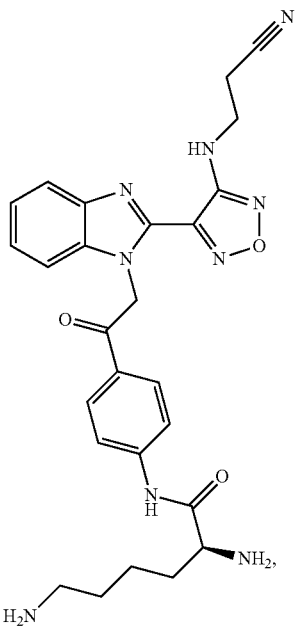 [SMILES: N#CCCNc1nonc1-c1nc2ccccc2n1CC(=O)c1ccc(NC(=O)[C@@H](N)CCCCN)cc1]

-continued
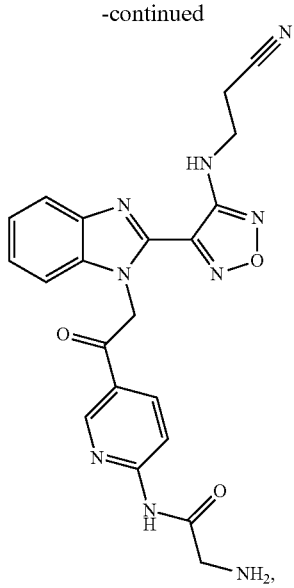
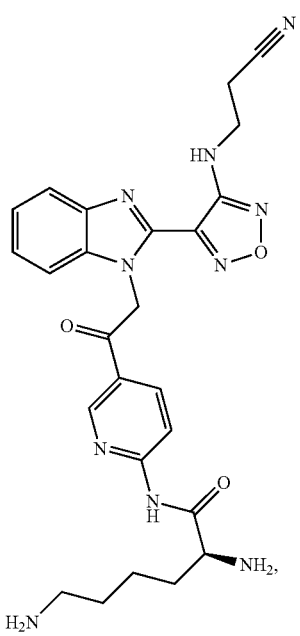 [SMILES: N#CCCNc1nonc1-c1nc2ccccc2n1CC(=O)c1ccc(NC(=O)[C@@H](N)CCCCN)cc1]
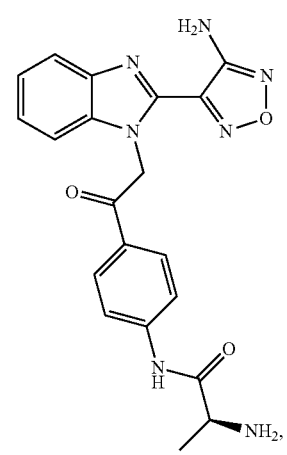
-continued
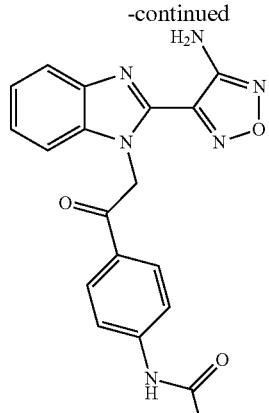
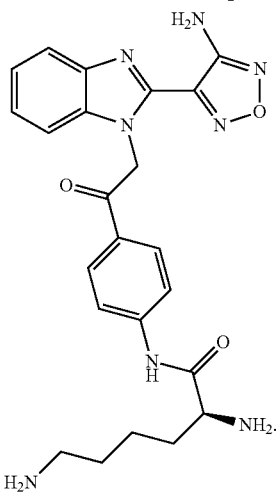
6. The compound of claim 4 wherein R$^1$ is cyanoethyl.
7. The compound of claim 6 selected from the group consisting of the compounds of formulae
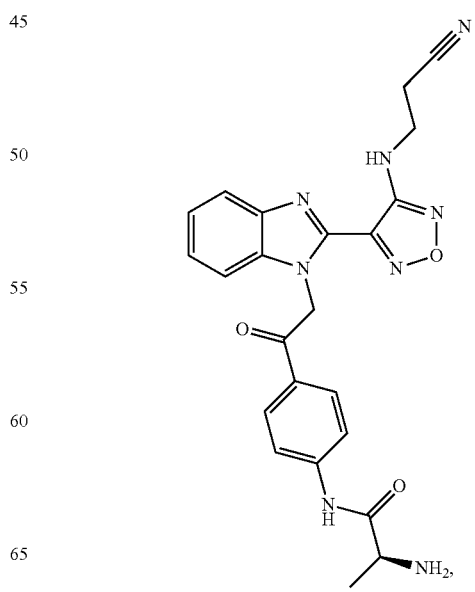

-continued
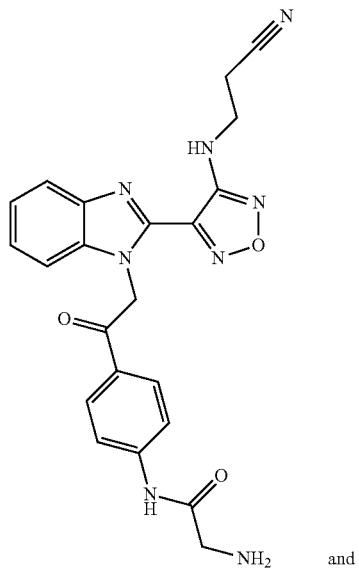 and
8. The compound of claim 2 having the formula
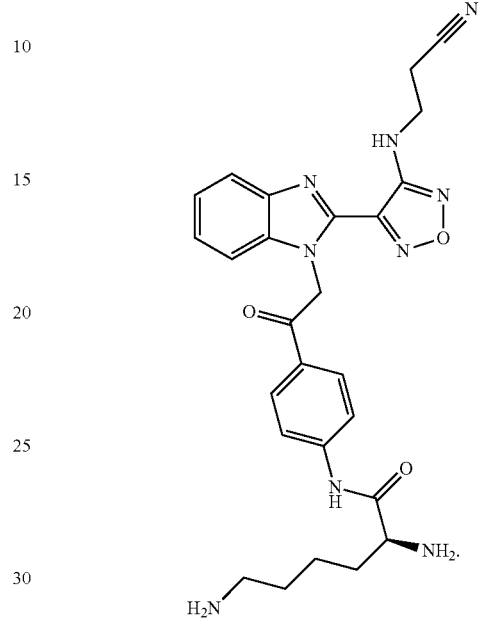
9. The compound of claim 1 which is a pharmaceutically acceptable salt of the compound of formula
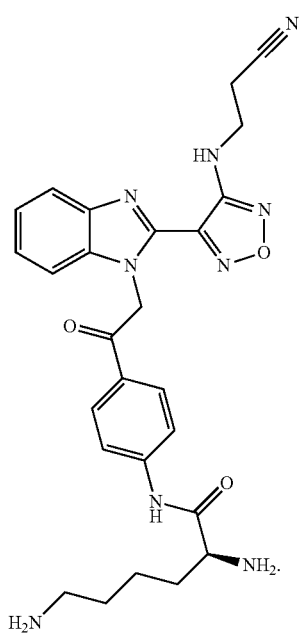
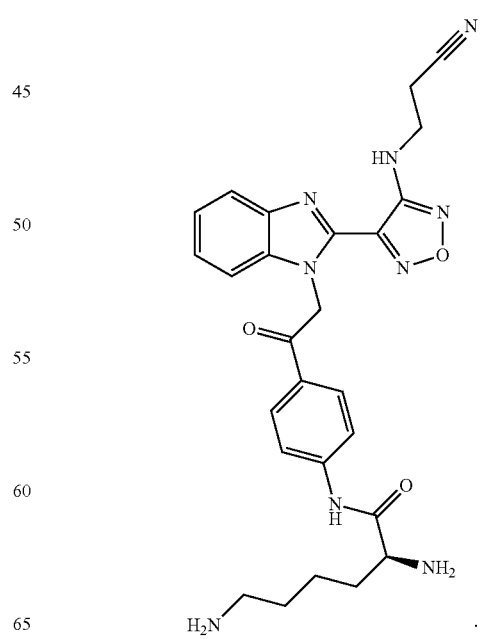

10. A process for the preparation of a compound of formula (II) as claimed in claim 1, comprising the steps that:
(1) a compound of formula (I-II)

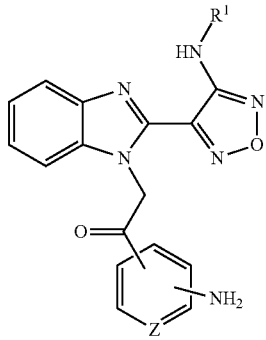
(I-II)

wherein
R¹ and the group

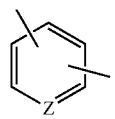

are as in claim 1; or
a derivative of such a compound comprising functional groups in protected form,
or a salt thereof is acylated with an amino acid of formula (III)

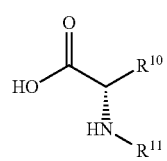
(III)

wherein
$R^{10}$ is selected from hydrogen (Gly), methyl (Ala) and protected aminobutyl (amino-protected Lys) and
$R^{11}$ is an amino protecting group, and
(2) any protecting groups in a protected derivative of the resulting compound are removed to yield a compound of formula (II) or a salt thereof and, if so desired,
(3) the obtained compound of formula (II) is converted to a salt or the obtained salt of the compound of formula (II) is converted to the compound of formula (II).

11. A process for the manufacture of a compound of formula (II-G):

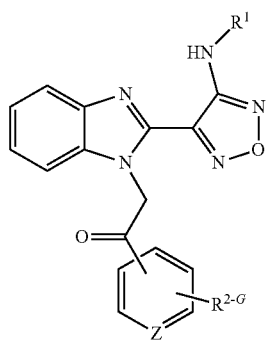
(II-G)

or a salt thereof, comprising the steps:
(a) reacting a compound of formula

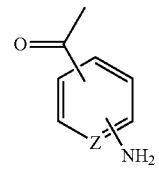

with an alpha-amino acid derivative of the formula:

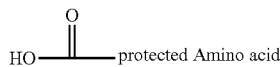

in the presence of an activating agent and optionally in the presence of suitable bases, catalysts or co-reagents to yield the compound of formula:

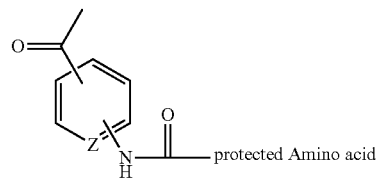

(b) reacting the product of Step (a) with a bromination agent to yield the bromo compound of formula:

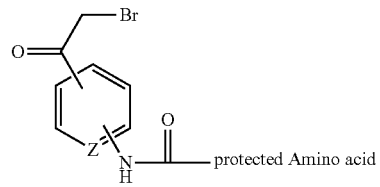

(c) reacting said bromo compound obtained in Step (b) with a compound of formula:

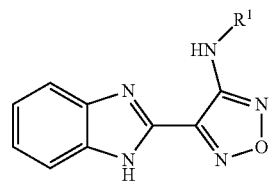

to yield the compound of formula:

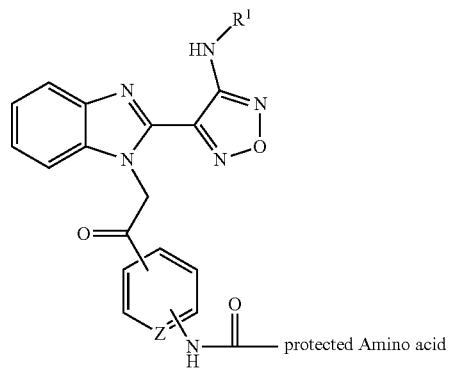

(d) removing any protection groups being present from the group "protected Amino acid" to yield the compound of formula (II-G) and, optionally,
(e) converting said compound of formula (II-G) to a salt thereof, in which formulae R$^1$ represents hydrogen, lower alkylcarbonyl, hydroxy-lower alkyl or cyano-lower alkyl,

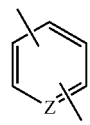

represents 1,4-phenylene or a group of formula

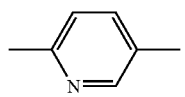

R$^{2-G}$ is a group of formula

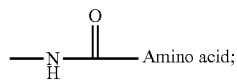

"Amino acid" represents a residue derived from a natural alpha-amino acid selected from glycine, alanine, and lysine by removing the carboxyl group from the alpha-carbon atom of said amino acid; and "protected Amino acid" means the same amino acid as "Amino acid", primary amino groups and if required also other functional groups of said amino acid however being protected by a protecting group.

12. A process according to claim 11, wherein
"Amino acid" represents lysine.

13. A compound of claim 1 for use as a medicament.

14. A compound according to claim 1 for the treatment of a solid neoplastic disease.

15. A pharmaceutical composition comprising a compound of formula (II) or a pharmaceutically acceptable salt thereof as claimed in claim 1 and a pharmaceutically acceptable, inert carrier.

16. A pharmaceutical composition according to claim 15, which is an aqueous solution.

17. A pharmaceutical composition according to claim 15, which is soluble in an aqueous carrier.

18. A composition according to claim 15 which is a composition for parenteral administration.

19. The process of claim 10 wherein the salt is a hydrochloride salt.

20. The compound of claim 9 wherein the pharmaceutically acceptable salt is a hydrochloride salt.

* * * * *